(12) United States Patent
Lampropoulos et al.

(10) Patent No.: US 11,717,664 B2
(45) Date of Patent: Aug. 8, 2023

(54) HEMOSTASIS VALVES HAVING MULTIPLE SEALABLE OPENINGS

(71) Applicant: Merit Medical Systems, Inc., South Jordan, UT (US)

(72) Inventors: Fred Lampropoulos, Salt Lake City, UT (US); Jim Mottola, West Jordan, UT (US); Mark Garcia, Wilmington, DE (US); Ronald Caputo, Manlius, NY (US)

(73) Assignee: Merit Medical Systems, Inc., South Jordan, UT (US)

( * ) Notice: Subject to any disclaimer, the term of this patent is extended or adjusted under 35 U.S.C. 154(b) by 232 days.

(21) Appl. No.: 16/056,795

(22) Filed: Aug. 7, 2018

(65) Prior Publication Data

US 2019/0046781 A1 Feb. 14, 2019

Related U.S. Application Data

(60) Provisional application No. 62/659,766, filed on Apr. 19, 2018, provisional application No. 62/572,258, (Continued)

(51) Int. Cl.
*A61M 39/06* (2006.01)
*A61M 39/20* (2006.01)
(Continued)

(52) U.S. Cl.
CPC ........ *A61M 39/0613* (2013.01); *A61M 39/20* (2013.01); *A61M 39/22* (2013.01); (Continued)

(58) Field of Classification Search
CPC .............. A61M 39/06; A61M 39/0613; A61M 39/0693; A61M 39/22; A61M 39/0606; (Continued)

(56) References Cited

U.S. PATENT DOCUMENTS

| 4,610,665 A | * | 9/1986 | Matsumoto | ....... A61M 39/0606 604/167.04 |
| 5,911,710 A | * | 6/1999 | Barry | ................ A61M 39/0693 604/167.04 |

(Continued)

FOREIGN PATENT DOCUMENTS

| EP | 2226027 | 9/2010 |
| JP | 2001299930 | 10/2001 |

OTHER PUBLICATIONS

International Search Report and Written Opinion dated Feb. 11, 2019 for PCT/US2018/045514.
(Continued)

*Primary Examiner* — Emily L Schmidt
*Assistant Examiner* — Alexandra Lalonde
(74) *Attorney, Agent, or Firm* — Dorsey & Whitney LLP

(57) ABSTRACT

Hemostasis valves and hemostasis valve systems are provided. A hemostasis valve can include a valve member, wherein the valve member includes a first sealable opening disposed through a first portion of the valve member and a second sealable opening disposed through a second portion of the valve member. The valve member may also include three or more sealable openings. A hemostasis valve system may include a hemostasis valve and another medical device. The hemostasis valve may be releasably coupleable to the other medical device.

18 Claims, 15 Drawing Sheets

Related U.S. Application Data filed on Oct. 13, 2017, provisional application No. 62/542,469, filed on Aug. 8, 2017.

(51) Int. Cl.
    *A61M 39/22*     (2006.01)
    *A61M 39/02*     (2006.01)

(52) U.S. Cl.
    CPC ............... *A61M 2039/0205* (2013.01); *A61M 2039/062* (2013.01); *A61M 2039/064* (2013.01); *A61M 2039/229* (2013.01); *A61M 2205/0216* (2013.01); *A61M 2205/6081* (2013.01)

(58) Field of Classification Search
    CPC .. A61M 2039/0633; A61M 2039/0686; A61M 2039/0626; A61M 2039/062; A61M 2039/064; A61M 2039/0646; A61M 2039/0653; A61M 2039/066; A61M 2039/0666; A61M 2039/0673; A61M 2039/068; A61M 2039/2426; A61M 29/00; A61M 39/20; A61M 39/0205; A61M 2205/0216; A61M 2205/6081; A61M 2039/0205; A61B 2017/3466; A61B 2017/3449; A61B 2017/3411; A61B 2017/3445; A61B 90/92; A61B 90/94; A61B 17/3462; A61B 2017/3464

See application file for complete search history.

(56) References Cited

U.S. PATENT DOCUMENTS

| | | | |
|---|---|---|---|
| 6,217,555 B1 * | 4/2001 | Hart | A61B 17/3462 128/DIG. 26 |
| 10,321,933 B1 * | 6/2019 | Ramee | A61M 39/0606 |
| 2005/0010238 A1 | 1/2005 | Potter et al. | |
| 2006/0211992 A1 * | 9/2006 | Prosek | A61B 17/3421 604/167.06 |
| 2008/0071221 A1 | 3/2008 | Rickerd | |
| 2009/0221966 A1 | 9/2009 | Richard | |
| 2010/0274093 A1 * | 10/2010 | Shelton, IV | A61B 17/3423 600/206 |
| 2012/0271116 A1 | 10/2012 | Koehler | |
| 2014/0188216 A1 | 7/2014 | Bishop et al. | |
| 2015/0065806 A1 * | 3/2015 | Cooper | A61B 17/3462 600/204 |
| 2015/0305863 A1 * | 10/2015 | Gray | A61F 2/962 623/2.11 |
| 2017/0056064 A1 | 3/2017 | Zergiebel et al. | |

OTHER PUBLICATIONS

European Search Report dated Sep. 23, 2021 for EP18843933.5.
European Examination Report dated Apr. 3, 2023 for EP18843933.5.

\* cited by examiner

HEMOSTASIS VALVES HAVING MULTIPLE SEALABLE OPENINGS

RELATED APPLICATIONS

This application claims priority to U.S. Provisional Application No. 62/542,469, filed on Aug. 8, 2017, titled "Hemostasis Valves Having Multiple Sealable Openings", and to U.S. Provisional Application No. 62/572,258 filed on Oct. 13, 2017, titled "Hemostasis Valves Having Multiple Sealable Openings", and to U.S. Provisional Application No. 62/659,766, filed on Apr. 19, 2018, titled "Hemostasis Valves Having Multiple Sealable Openings", which are hereby incorporated by reference in their entirety.

TECHNICAL FIELD

The present disclosure relates generally to hemostasis valves. More specifically, the present disclosure relates to hemostasis valves configured for passage of two or more elongate medical devices. This disclosure also relates to hemostasis valve systems including a hemostasis valve and a medical device such as a sheath introducer, wherein the hemostasis valve is coupleable to the medical device. Related methods are also disclosed.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

Figure 1A:
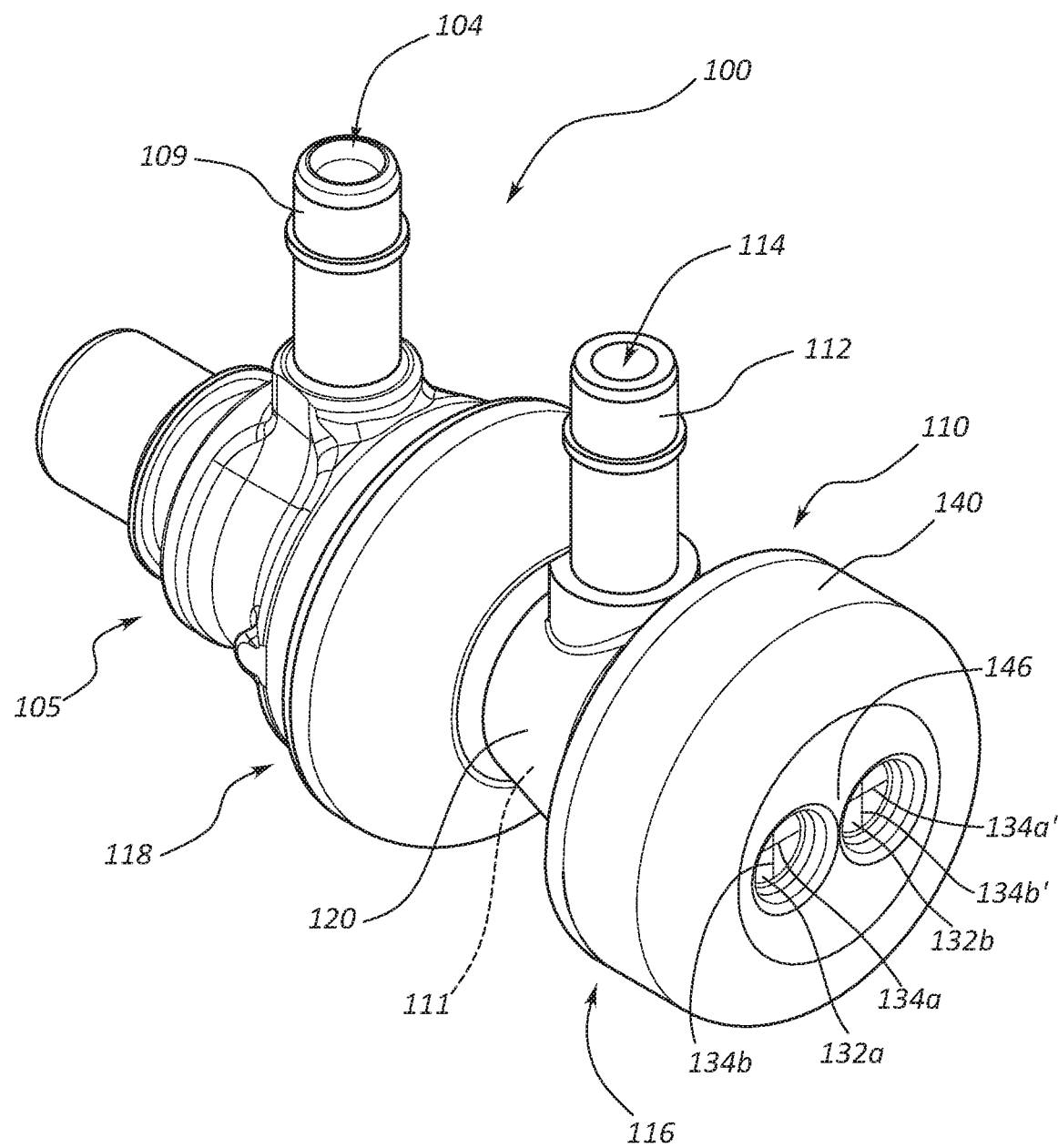
FIG. 1A is a perspective view of a hemostasis valve system.

The various embodiments disclosed herein generally relate to hemostasis valves and hemostasis valve systems. In some embodiments, the hemostasis valve includes a valve member, wherein the valve member includes a first sealable opening disposed through a first portion of the valve member and a second sealable opening disposed through a second portion of the valve member. The valve member may also include three or more sealable openings. In certain embodiments, a hemostasis valve system may include a hemostasis valve and a first medical device (e.g., a sheath introducer). The hemostasis valve may be releasably coupleable to the first medical device.

Various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of a hemostasis valve is defined as the end closest to the practitioner during utilization of the hemostasis valve. The distal end is the end opposite the proximal end, along the longitudinal direction of the hemostasis valve.

The term "resilient" refers to a component, device, or object having a particular shape that can then be elastically deformed into a different shape, but that may return to the original shape when unconstrained. For example, a wall of a valve member may have a first shape when unconstrained (i.e., when not engaged with an elongate medical device) and, in use, the wall may then be constrained (i.e., temporarily engaged with the elongate medical device) to elastically deform the wall into a second shape (i.e., displaced laterally due to interaction with a portion of the elongate medical device), then unconstrained (i.e., removed from engagement with the elongate medical device) such that the wall returns to its first shape or substantially returns to its first shape.

Various examples of hemostasis valve systems described herein comprise sealable openings configured to allow passage of instruments through a valve while maintaining hemostasis across the valve. Various examples herein reference sealable openings comprising one or more slits in a valve member. Notwithstanding any specific example to slits herein, sealable openings within the scope of this disclosure include single slits, intersecting slits, expandable holes, pin holes, multi-diameter holes, and so forth. Accordingly, any suitable sealable opening may be used in connection with the specific embodiments described herein.

Figure 1B:
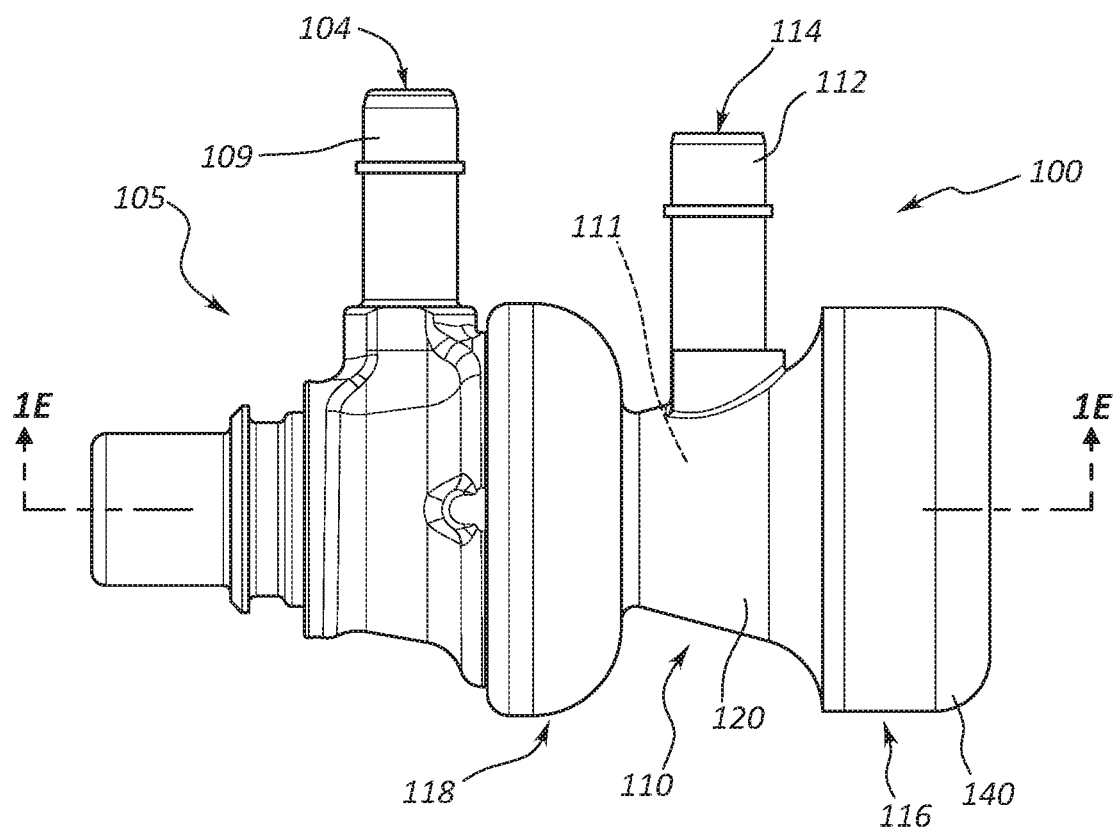
FIG. 1B is a side view of the hemostasis valve system of FIG. 1A.
Figure 1C:
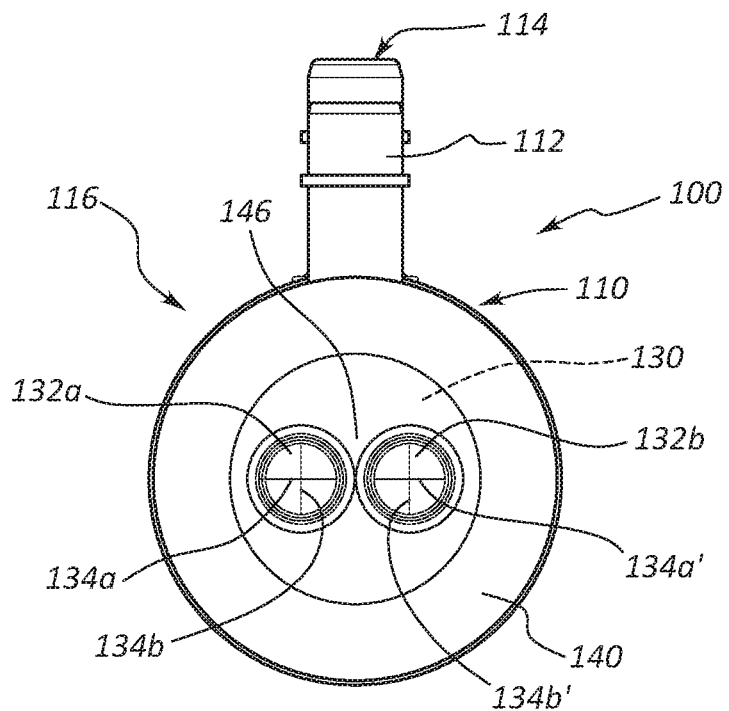
FIG. 1C is an end view of a proximal end portion of the hemostasis valve system of FIG. 1A.

FIG. 1A is a perspective view of a hemostasis valve system 100, FIG. 1B is a side view of the hemostasis valve system 100, and FIG. 1C is an end view of a proximal end portion 116 of the hemostasis valve system 100. The hemostasis valve system 100 can include a hemostasis valve 110 and another medical device such as first medical device 105. The hemostasis valve 110 can be releasably coupleable to the first medical device 105. In various embodiments, the first medical device 105 may be a valved medical device (e.g., a traditional hemostasis valve, a valved sheath introducer, etc.). Other suitable first medical devices 105 are also within the scope of this disclosure. In certain embodiments, the hemostasis valve 110 is independent of the hemostasis valve system 100. For example, the hemostasis valve 110 may be provided and/or used without the first medical device 105 or any other component of the hemostasis valve system 100 as provided herein. Furthermore, the hemostasis valve 110 may be configured for universal adaption. That is, the hemostasis valve 110 may be coupleable to a first medical device 105 of any suitable size. For example, the first medical device 105 may be an introducer having a size between about 4 French and about 8.5 French, and the hemostasis valve 110 may be coupleable to the introducer.

Figure 1D:
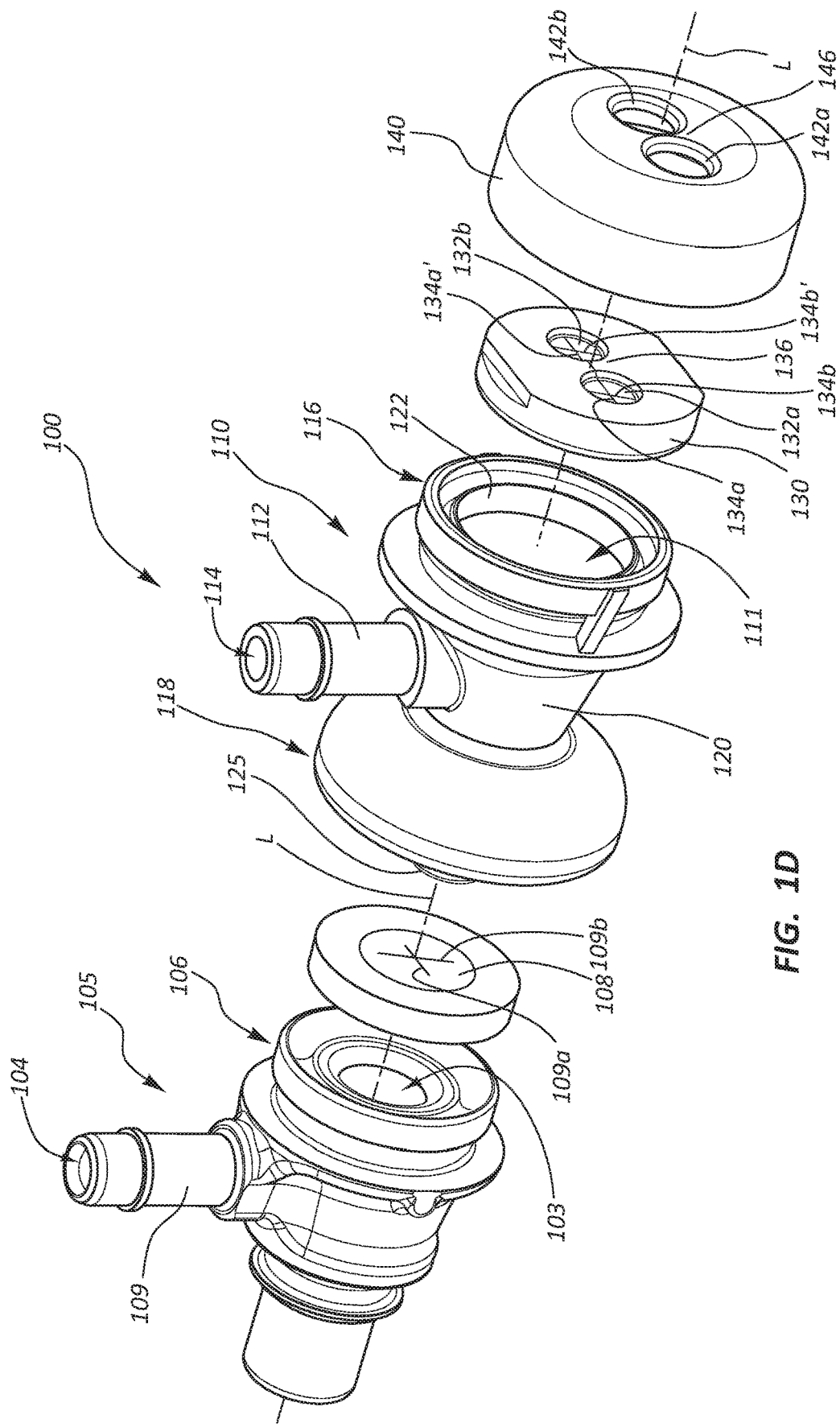
FIG. 1D is an exploded view of the hemostasis valve system of FIG. 1A.
Figure 1E:
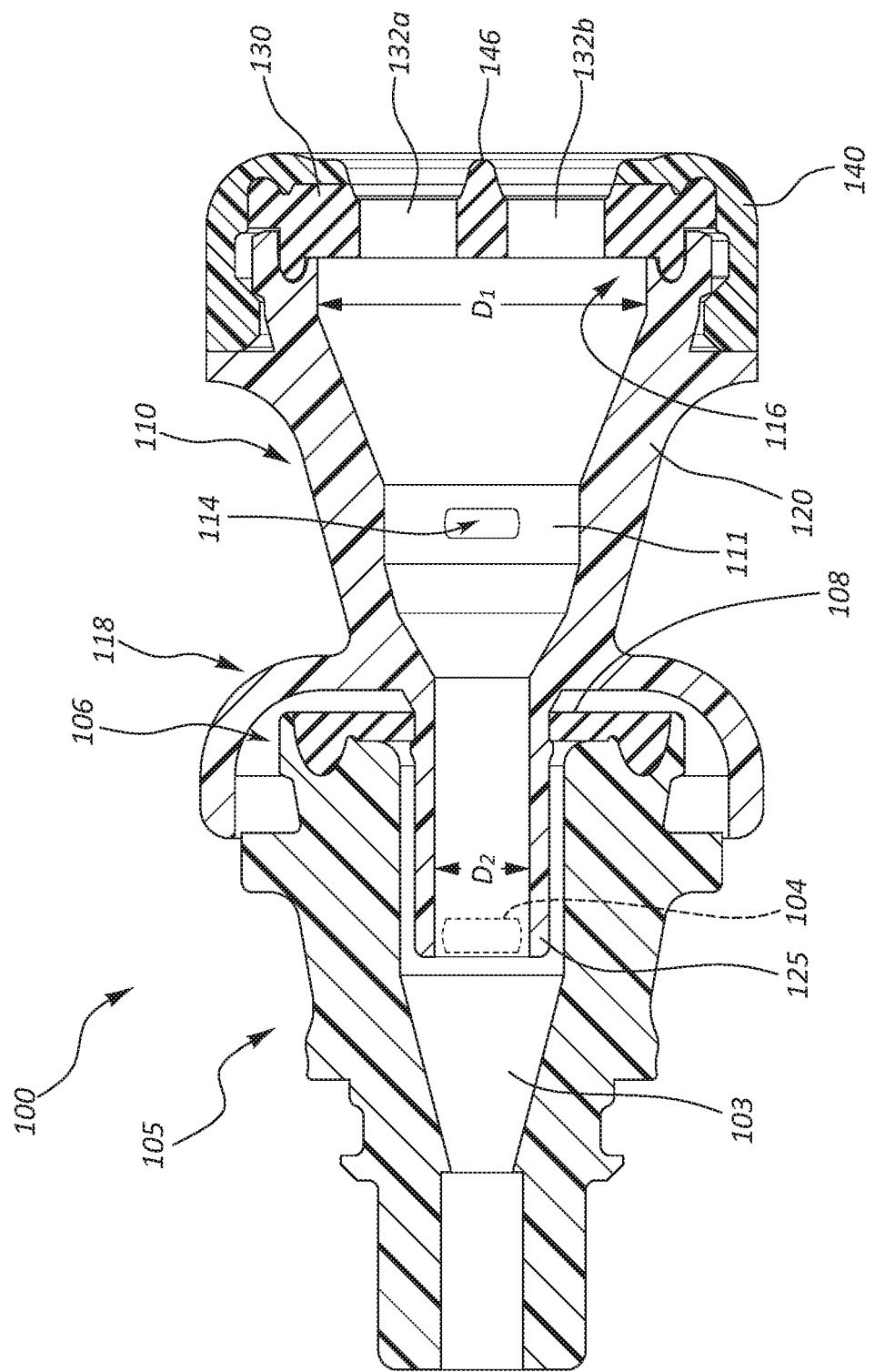
FIG. 1E is a cross-sectional view of the hemostasis valve system of FIG. 1B taken through line 1E-1E.

In some embodiments, the hemostasis valve 110 can include a body 120 and a valve member 130 (see also FIGS. 1D and 1E). The valve member 130, or at least a portion of the valve member 130, may be formed from a resilient material or a stretchable material. For example, the valve member 130 may be formed from an elastomeric material. The valve member 130 can be coupled to the body 120 at a position at or adjacent the proximal end portion 116 of the body 120.

In certain embodiments, the hemostasis valve 110 can further include a cap 140. The cap 140 may be coupled to the body 120 such that at least a portion of the valve member 130 is disposed between at least a portion of the body 120 and at least a portion of the cap 140. For example, the cap 140 may secure the valve member 130 to the body 120. The cap 140 may be releasably coupleable to the body 120. For example, a practitioner may desire to remove the cap 140 to access the valve member 130. In various embodiments, the practitioner may desire to access the valve member 130, for example, to replace the valve member 130, to clean the valve member 130, etc. In various embodiments, the cap 140 may provide protection to at least a portion of the valve member 130. For example, the cap 140 may be formed from a rigid material and the cap 140 may limit or prevent at least a portion of the valve member 130 from being compromised or damaged (e.g., upon contact with a surface, a body part, another medical device, etc.). In various other embodiments, the hemostasis valve 110 may lack the cap 140. The valve member 130 may comprise a swabable or cleanable surface with or without the cap 140.

In some embodiments, the hemostasis valve 110, or at least a portion of the hemostasis valve 110, may be formed from a clear or transparent material. Accordingly, a color of a portion (e.g., an end) of an introducer that is coupled to the hemostasis valve 110 may be visible (e.g., to a practitioner) through at least a portion of the hemostasis valve 110. In certain embodiments, the color of the end of the introducer may correspond to the size (e.g., the French size) of the introducer.

In various embodiments, the hemostasis valve 110, or at least a portion of the hemostasis valve 110, may include one or more indicia. The indicium may be a color. The one or more indicia of the hemostasis valve 110, or at least a portion of the hemostasis valve 110, may communicate a size of the hemostasis valve 110 to a user. For example, the hemostasis valve 110, or at least a portion of the hemostasis valve 110, may be blue and the blue color may correspond to a size of 8.5 French, which may indicate to a user that two or more elongate medical devices may be disposed through the hemostasis valve 110 that add up to a total of 8 French (e.g., two 4 French catheters, a 2 French catheter and a 6 French catheter, etc.). Other suitable colors and corresponding sizes are also within the scope of this disclosure. In some embodiments, the hemostasis valve 110 may be a neutral color, including clear or white.

In some embodiments, the valve member 130 may include a first sealable opening 132a disposed through a first portion of the valve member 130. As shown, the valve member 130 may also include a second sealable opening 132b disposed through a second portion of the valve member 130. The first and second portions of the valve member 130 may be adjacent to each other (e.g., as shown in FIGS. 1A and 1C), or the first and second portions of the valve member 130 may be spaced apart from each other. Other suitable dispositions of the first and second portions of the valve member 130 are also within the scope of this disclosure. In some circumstances, a practitioner may desire to access and/or treat two branches of a vessel (e.g., simultaneously or sequentially). As further discussed herein, a hemostasis valve having two or more sealable openings, as disclosed herein, may aid in such access and/or treatment.

Furthermore, the first sealable opening 132a may include a first slit 134a disposed through at least a portion of the first sealable opening 132a and/or along at least a portion of the diameter of the first sealable opening 132a. The first sealable opening 132a may also include a second slit 134b, wherein the second slit 134b may intersect at least a portion of the first slit 134a. Likewise, the second sealable opening 132b may include the first slit 134a' disposed through at least a portion of the second sealable opening 132b and/or along at least a portion of the diameter of the second sealable opening 132b. The second sealable opening 132b may also include a second slit 134b', wherein the second slit 134b' may intersect at least a portion of the first slit 134a'. As depicted, the first slits 134a, 134a' may be disposed substantially perpendicular to the second slits 134b, 134b'. The first slit 134a may be continuous with the first slit 134a' (see FIG. 1D). Stated another way, the first slit 134a can be integral with the first slit 134a'. In some other embodiments, the first slit 134a and the first slit 134a' may be separate or distinct slits. In certain embodiments, the valve member 130 may include a third sealable opening, a fourth sealable opening, a fifth sealable opening, a sixth sealable opening, a seventh sealable opening, an eighth sealable opening, or more sealable openings.

The sealable openings (e.g., the first sealable opening 132a and the second sealable opening 132b) may be configured such that an elongate medical device (e.g., a guidewire, a stylet, a catheter, etc.) may be disposed through at least a portion of the slits of the sealable opening, and the sealable opening and/or the slits may form a seal (e.g., a hemostatic seal) around the elongate medical device. In some embodiments, the sealable openings, or at least a portion of each of the sealable openings, may be formed from a resilient or stretchable material such that the sealable opening and/or the slits of the sealable opening may form a seal (e.g., around an outside surface of an elongate medical device). The sealable openings may also be configured such that the sealable openings are substantially sealed when no object (e.g., an elongate medical device) is disposed through the sealable openings. An elongate medical device may be disposed through the first sealable opening 132a and then the elongate medical device may be transitioned along at least a portion of the first slits 134a, 134a' (e.g., when the first slits 134a, 134a' are integral) such that the elongate medical device is disposed through the second sealable opening 132b, or vice versa.

With continued reference to FIGS. 1A-1C, the hemostasis valve 110 may further include a sidearm 112. The sidearm 112 may include a sidearm lumen 114, the sidearm lumen 114 extending through at least a portion of the sidearm 112. In some embodiments, the sidearm lumen 114 may be in fluid communication with a lumen or a hemostasis valve lumen 111 of the hemostasis valve 110 (see also FIGS. 1D and 1E). Accordingly, a practitioner may dispose or introduce a fluid through the sidearm lumen 114 to flush and/or clean at least a portion of the hemostasis valve lumen 111.

The first medical device 105 may also include a sidearm 109. The sidearm 109 may include a sidearm lumen 104, the sidearm lumen 104 extending through at least a portion of the sidearm 109. In some embodiments, the sidearm lumen 104 may be in fluid communication with a lumen or a first medical device lumen 103 of the first medical device 105 (see also FIGS. 1D and 1E). Accordingly, a practitioner may dispose or introduce a fluid through the sidearm lumen 104 to flush and/or clean at least a portion of the first medical device lumen 103. The sidearm 112 may rotate independent of the sidearm 109, for example, when the hemostasis valve 110 is coupled to the first medical device 105. Furthermore, the hemostasis valve 110 may be configured such that upon coupling of the hemostasis valve 110 to the first medical device 105, the sidearm lumen 104 is not blocked by a portion of the hemostasis valve 110. For example, fluid communication through the sidearm lumen 104 may be substantially maintained upon coupling of the hemostasis valve 110 to the first medical device 105. In various embodiments, each of the sidearm lumens 104, 114 may be in fluid communication with each of the first medical device lumen 103 and the hemostasis valve lumen 111 (e.g., when the first medical device 105 is coupled to the hemostasis valve 110).

The hemostasis valve 110 may also include a coupling member (not shown) disposed, for example, at or adjacent a distal end portion 118 of the hemostasis valve 110. The coupling member may be configured to couple, or releasably couple, the hemostasis valve 110 to the first medical device 105. In certain embodiments, the coupling member may be configured to form a snap fit between the hemostasis valve 110 and the first medical device 105. In certain other embodiments, the coupling member may be configured to threadably couple the hemostasis valve 110 and the first medical device 105 to each other (e.g., the coupling member may include one or more threads). Other suitable coupling mechanisms are also within the scope of this disclosure.

FIG. 1D is an exploded view of the hemostasis valve system 100. As shown, the hemostasis valve system 100 can include the hemostasis valve 110. As discussed above, the hemostasis valve 110 can include the body 120 and the sidearm 112 extending radially outward relative to a longitudinal axis L of the hemostasis valve 110.

As shown, the hemostasis valve lumen 111 can extend between the proximal end portion 116 and the distal end portion 118 of the hemostasis valve 110. Accordingly, there may be fluid communication between the proximal end portion 116 and the distal end portion 118 of the hemostasis valve 110.

The hemostasis valve 110 can further include the valve member 130, wherein the valve member 130 is configured to be disposed at or adjacent the proximal end portion 116 of the hemostasis valve 110. Stated another way, the valve member 130 may be coupleable to the hemostasis valve 110 at a position at or adjacent the proximal end portion 116 of the hemostasis valve 110 (e.g., at a valve member coupling portion 122). The valve member coupling portion 122 may be configured to limit or prevent movement (e.g., longitudinal movement) of the valve member 130 relative to the hemostasis valve 110 when the valve member 130 is coupled to the hemostasis valve 110. For example, the valve member coupling portion 122 may include one or more ridges which engage or interact with at least a portion of the valve member 130 such that the valve member 130 is secured to the hemostasis valve 110. The valve member coupling portion 122 may also be configured to limit or prevent leakage around an edge of the valve member 130. For example, the valve member coupling portion 122 may form a seal around at least a portion of the valve member 130 (i.e., between the body 120 and the valve member 130) when the valve member 130 is coupled to the body 120.

As depicted, the valve member 130 includes the first sealable opening 132a disposed through a first portion of the valve member 130 and the second sealable opening 132b disposed through a second portion of the valve member 130. Additionally, each of the first and second sealable openings 132a, 132b includes the first slits 134a, 134a' and the second slits 134b, 134b', respectively, disposed through at least a portion of the first and second sealable openings 132a, 132b. The valve member 130 can further include a wall or a flow divider 136 disposed between the first sealable opening 132a and the second sealable opening 132b. As illustrated, the first slits 134a, 134a' can extend through the wall 136 between each of the first and second sealable openings 132a, 132b. At least a portion of the wall 136 may be resilient or deformable (e.g., at least a portion of the wall 136 may be formed from a resilient material). In some embodiments, the wall 136 may be resilient such that it may bias away from the first sealable opening 132a toward the second sealable opening 132b, or vice versa. The resilient wall 136 may be configured to release pressure on at least a portion of the valve member 130, for example, upon displacement of an elongate medical device through the first and/or the second sealable opening 132a, 132b.

In some embodiments, the wall 136 may be displaceable between at least a resting position, a first lateral position, and a second lateral position. As such, the wall 136 may be disposed in the resting position (e.g., as depicted in FIG. 1D) when the wall 136 is not engaged with an object such as an elongate medical device disposed through one of the sealable openings 132a, 132b. Interaction between the wall 136 and an object may displace (e.g., laterally displace) at least a portion of the wall 136. For example, displacement of an elongate medical device through the first sealable opening 132a may exert a force on the wall 136 such that at least a portion of the wall 136 is displaced laterally away from the first sealable opening 132a. Stated another way, in such a configuration the wall 136 may transition from the resting position to the second lateral position. Analogously, displacement of an elongate medical device through the second sealable opening 132b may exert a force on the wall 136 such that at least a portion of the wall 136 is displaced laterally away from the second sealable opening 132b. In other words, in such a configuration the wall 136 may transition from the resting position to the first lateral position.

Likewise, the sealable openings (e.g., the first and second sealable openings 132a, 132b) may have a resting configuration and a non-resting configuration. That is, a sealable opening may be in the resting configuration when the sealable opening is not biased or stretched (e.g., due to an interaction with an object such as an elongate medical device). The first and second sealable openings 132a, 132b, as illustrated in FIG. 1D, are in the resting configuration. Upon interaction with an object, however, the sealable openings may transition from the resting configuration to the non-resting configuration. In the non-resting configuration the sealable openings may be biased, deformed, and/or stretched.

Upon displacement of the wall 136 a size of the first sealable opening 132a can decrease as a size of the second sealable opening 132b increases, or vice versa. Such a configuration may aid in the displacement of elongate medical devices having different profiles or sizes (e.g., larger profiles relative to the size of the first or second sealable opening 132a, 132b in the resting configuration) through the first and second sealable openings 132a, 132b. For example, a practitioner may desire to displace a first elongate medical device having a first profile through the first sealable opening 132a. The first profile, however, may be greater than a size of the first sealable opening 132a when the first sealable opening 132a is in the resting configuration. Accordingly, the practitioner may displace the wall 136 from the resting position to the second lateral position such that the size of the first sealable opening 132a increases and displacement of the first elongate medical device through the first sealable opening 132a is allowed or permitted.

Also depicted in FIG. 1D is the cap 140. The cap 140 can include a first cap opening 142a and a second cap opening 142b. The first cap opening 142a may be disposed through the cap 140 such that upon coupling of the cap 140 to the hemostasis valve 110, the first cap opening 142a is in substantial alignment with the first sealable opening 132a. Likewise, the second cap opening 142b may be disposed through the cap 140 such that upon coupling of the cap 140 to the hemostasis valve 110, the second cap opening 142b is in substantial alignment with the second sealable opening 132b. As noted above, the valve member 130 may include more than two sealable openings. Accordingly, in some embodiments, the cap 140 may include three, four, five, or more cap openings. A wall 146 can be disposed between the first and second cap openings 142a, 142b. In some embodiments, at least a portion of the wall 146 may be resilient or deformable. The wall 146 may be resilient such that it may bias away from the first cap opening 142a toward the second cap opening 142b, or vice versa. An elongate medical device may be disposed through the first cap opening 142a and the first sealable opening 132a and then the elongate medical device may be transitioned along at least a portion of the first slits 134a, 134a' such that the elongate medical device is disposed through the second sealable opening 132b, or vice versa. In such a configuration, the resilient wall 146 may bias such that the elongate medical device may transition between at least a portion of the each of the first and second sealable openings 132a, 132b. In some other embodiments, the hemostasis valve 110 may lack the cap 140 such that an elongate medical device may transition between the first and second sealable openings 132a, 132b without interacting with the wall 146.

At least a portion of an edge surrounding the first and/or the second cap opening 142a, 142b may be chamfered or sloped. Such a configuration may aid in guiding an elongate medical device through the first and/or the second cap opening 142a, 142b and through the first and/or the second sealable opening 132a, 132b.

The first and second sealable openings 132a, 132b can provide communication between the hemostasis valve lumen 111 and a position proximal of the hemostasis valve 110 (e.g., via the first slits 134a, 134a' and the second slits 134b, 134b'). For example, as discussed above, an elongate medical device may be disposed through at least a portion of the slits of the sealable opening such that access is provided to the hemostasis valve lumen 111 from a position outside of the hemostasis valve 110 (e.g., from a position proximal of the hemostasis valve 110).

The hemostasis valve system 100 may also include the first medical device 105. As illustrated, the distal end portion 118 of the hemostasis valve 110 may be shaped (e.g., skirt-shaped or otherwise shaped) such that upon coupling of the hemostasis valve 110 and the first medical device 105 at least a portion of the distal end portion 118 extends around at least a portion of a proximal end portion 106 of the first medical device 105. In certain embodiments, the first medical device 105 may include a valve 108; for example, the first medical device 105 may be a valved medical device. Furthermore, the hemostasis valve 110 may include a valve bypass portion 125, wherein the valve bypass portion 125 extends distally from the distal end portion 118 of the hemostasis valve 110. In some embodiments, the hemostasis valve lumen 111 may extend through at least a portion of the valve bypass portion 125.

The valve bypass portion 125 may be configured to bypass or override the valve 108 of the valved medical device 105 when at least a portion of the valve bypass portion 125 is disposed through at least a portion of the valve 108 of the valved medical device 105. For example, at least a portion of the valve bypass portion 125 may be configured to be displaced through the valve 108 (e.g., via slits 109a, 109b of the valve 108) and the valve 108 may be configured to form a seal (e.g., a hemostatic seal) around the valve bypass portion 125. Accordingly, the valve bypass portion 125 may be configured to couple the hemostasis valve 110 to the first medical device or valved medical device 105.

Upon coupling of the hemostasis valve 110 and the valved medical device 105, the hemostasis valve 110 may be in fluid communication with the valved medical device 105 (e.g., via the hemostasis valve lumen 111).

FIG. 1E is a cross-sectional view of the hemostasis valve system 100 through line 1E-1E of FIG. 1B. The hemostasis valve system 100 can include the hemostasis valve 110 and the first medical device 105. As discussed above, the hemostasis valve 110 can include the body 120 and the valve member 130. The valve member 130 can be coupled to the body 120 at a position at or adjacent the proximal end portion 116 of the body 120. The hemostasis valve 110 can further include the cap 140. The cap 140 may be coupled to the body 120 such that at least a portion of the valve member 130 is disposed between at least a portion of the body 120 and at least a portion of the cap 140.

As illustrated, the valve member 130 can include the first sealable opening 132a disposed through a first portion of the valve member 130 and the second sealable opening 132b disposed through a second portion of the valve member 130. The hemostasis valve 110 can further include the sidearm 112 (see FIGS. 1A-1D). The sidearm 112 may include the sidearm lumen 114, wherein the sidearm lumen 114 can extend through at least a portion of the sidearm 112. As depicted, the sidearm lumen 114 may be in fluid communication with at least a portion of the hemostasis valve lumen 111 of the hemostasis valve 110. The hemostasis valve lumen 111 can be shaped such that upon displacement of a first elongate medical device through the first sealable opening 132a, the first elongate medical device may be directed from a proximal end of the hemostasis valve lumen 111 toward a distal end of the hemostasis valve lumen 111. For example, as shown, the sides or inner surfaces of at least a portion of the hemostasis valve lumen 111 are sloped from a first, wider diameter $D_1$ at or adjacent the proximal end of the hemostasis valve lumen 111 to a second, narrower diameter $D_2$ at or adjacent the distal end of the hemostasis valve lumen 111. Likewise, the shape of the hemostasis valve lumen 111 can aid in the displacement of a second elongate medical device through the second sealable opening 132b from the proximal end of the hemostasis valve lumen 111 to the distal end of the hemostasis valve lumen 111.

As discussed above, the distal end portion 118 of the hemostasis valve 110 may be shaped such that upon coupling the hemostasis valve 110 and the first medical device 105 at least a portion of the distal end portion 118 extends around at least a portion of the proximal end portion 106 of the first medical device 105. In the illustrated embodiment, at least a portion of the distal end portion 118 is skirt-shaped. In some other embodiments, at least a portion of the distal end portion 118 may be conical, cap-shaped, or otherwise suitably shaped. Furthermore, the hemostasis valve 110 may include the valve bypass portion 125 extending distally from the distal end portion 118 of the hemostasis valve 110. As illustrated, the hemostasis valve lumen 111 can extend through at least a portion of the valve bypass portion 125.

With continued reference to FIG. 1E, at least a portion of the valve bypass portion 125 may be configured to be displaced through the valve 108 of the first medical device 105. As such, the valve bypass portion 125 may couple the hemostasis valve 110 to the first medical device or valved medical device 105. Upon coupling of the hemostasis valve 110 and the valved medical device 105, the hemostasis valve 110 may be in fluid communication with the valved medical device 105. In some embodiments, a distal end of the valve bypass portion 125 may be rounded such that the distal end of the valve bypass portion 125 is atraumatic (e.g., the distal end of the valve bypass portion 125 may be configured to avoid or limit damaging or traumatizing the valve 108 of the first medical device 105).

Figure 1F:
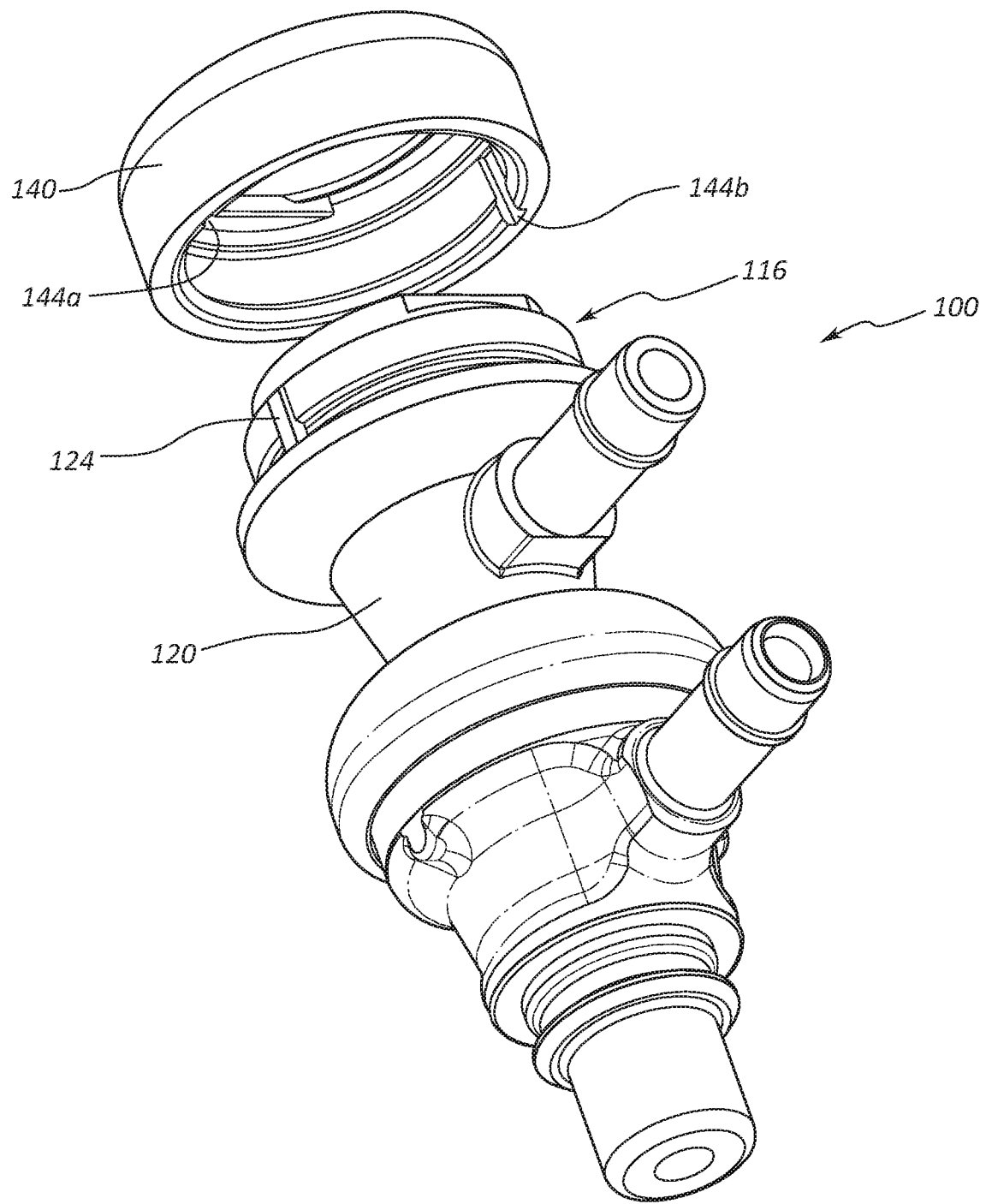
FIG. 1F is a partial exploded view of the hemostasis valve system of FIG. 1A.

FIG. 1F is a partial exploded view of the hemostasis valve system 100 showing a distal end of the cap 140. As depicted, the cap 140 may include two recessed portions 144a, 144b and the proximal end portion 116 of the body 120 may include a single raised portion 124. Caps with more or fewer recessed portions and raised portions are likewise within the scope of this disclosure. In the illustrated embodiment, the raised portion 124 extends radially outward from the proximal end portion 116 of the body 120. The recessed portion 144a may be disposed about 180° from the recessed portion 144b along the circumference of the cap 140, though other relative positions are within the scope of this disclosure. For example, in some other embodiments, the recessed portions 144a, 144b may be disposed about 30°, about 45°, about 90°, or another suitable number of degrees relative to each other and the cap 140 may comprise additional recessed portions, spaced equally or irregularly about the circumference of the cap 140.

The raised portion 124 may be configured to receive one of the recessed portions 144a, 144b. Upon coupling the cap 140 to the body 120, the recessed portion 144a or the recessed portion 144b may engage or interact with the raised portion 124. The engagement of the raised portion 124 with one of the recessed portions 144a, 144b can form a key/lock mechanism, such that when the cap 140 is coupled to the body 120, the cap 140 cannot be rotated relative to the body 120, or vice versa. Stated another way, the key/lock mechanism may "lock" the rotational position of the cap 140 in relation to the body 120. In some embodiments, the cap 140 may include one, three, four, five or another suitable number of recessed portions and the proximal end portion 116 of the body 120 may include two, three, four, five, or another suitable number of raised portions 124.

Figure 1G:
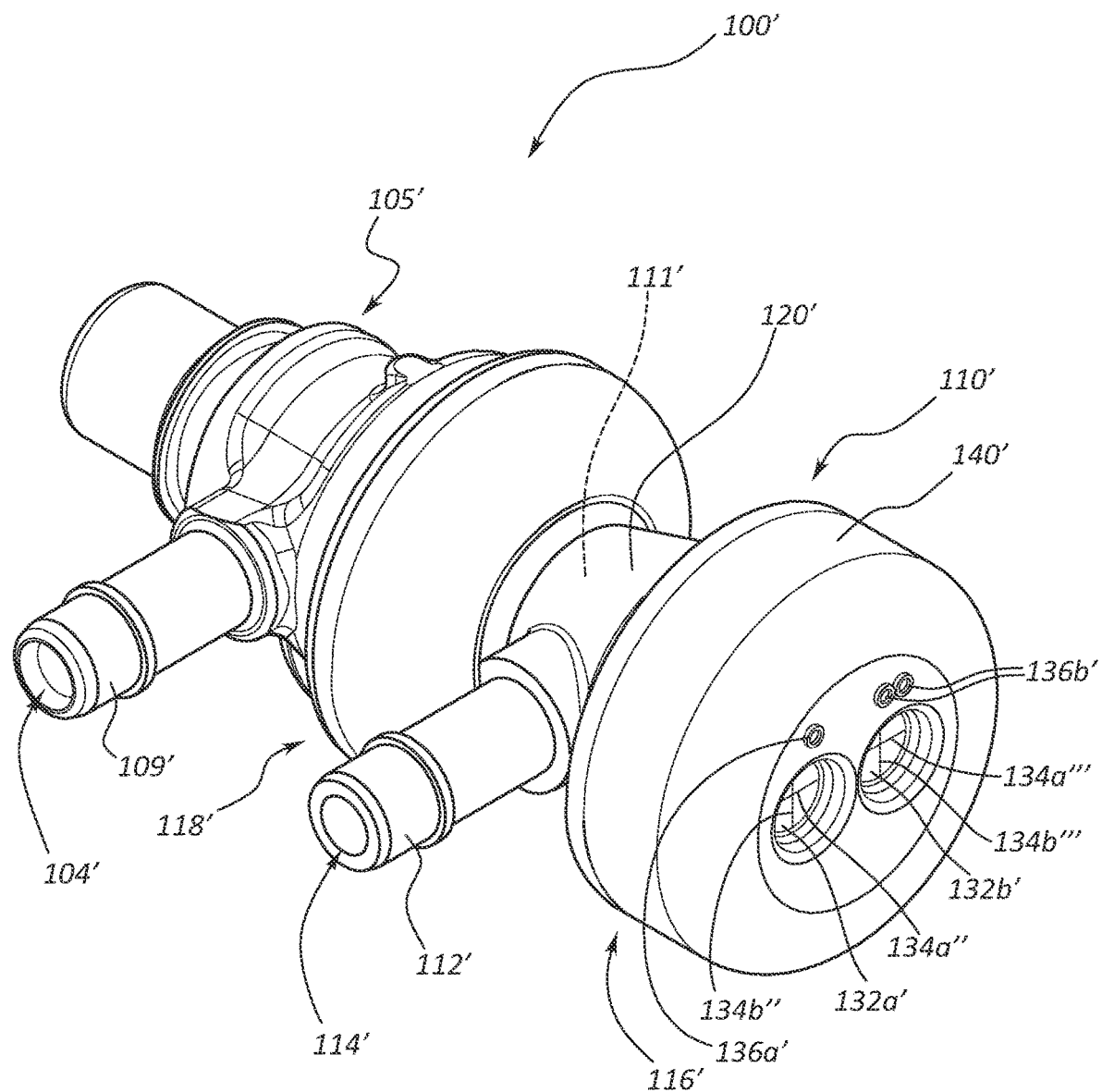
FIG. 1G is a perspective view another embodiment of a hemostasis valve system.
Figure 1H:
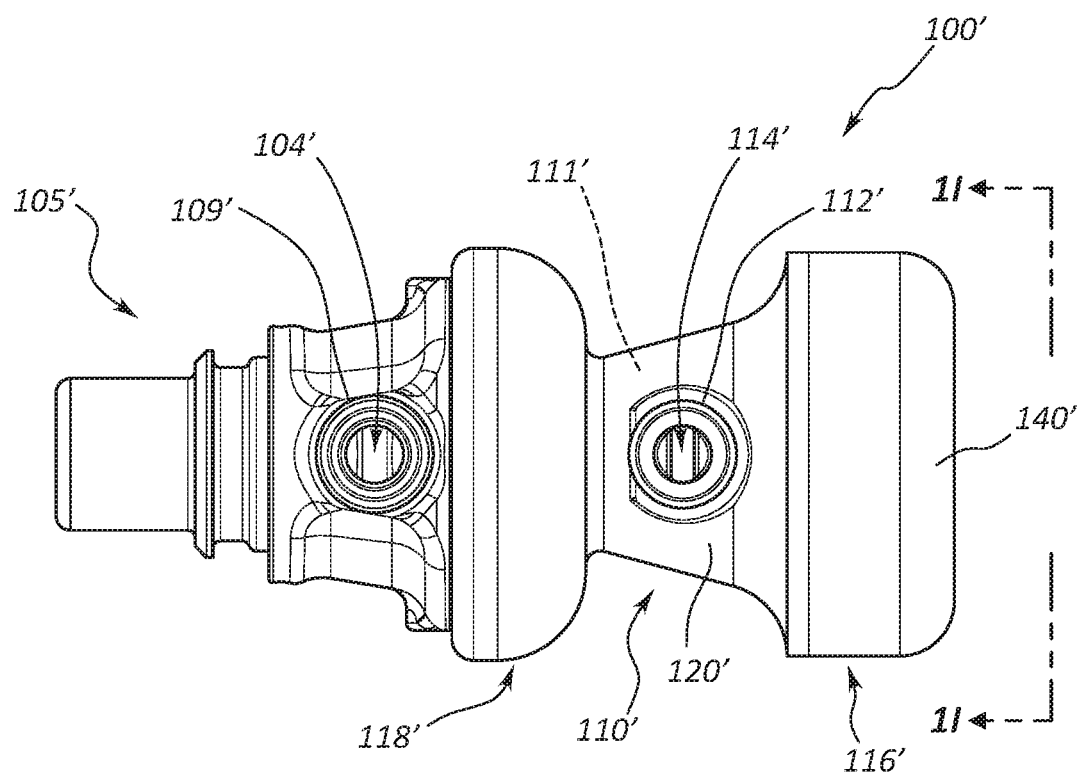
FIG. 1H is a side view of the hemostasis valve system of FIG. 1G.
Figure 1I:
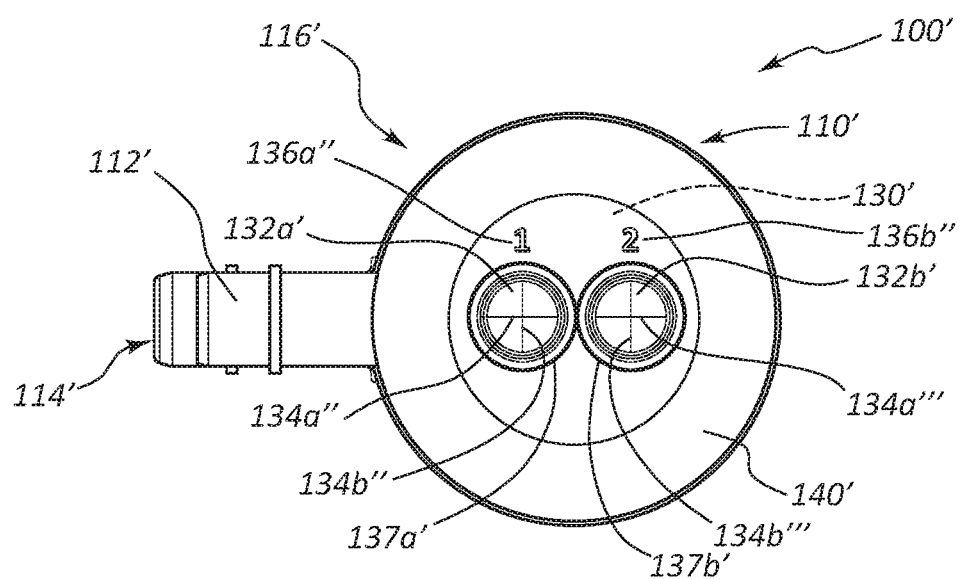
FIG. 1I is an end view of a proximal end portion of the hemostasis valve system of FIG. 1G, with alternate indicia.

FIG. 1G is a perspective view of a hemostasis valve system 100', FIG. 1H is a side view of the hemostasis valve system 100', and FIG. 1I is an end view of a proximal end portion 116' of the hemostasis valve system 100', with the variation that FIG. 1I illustrates alternate indicia as compared to the embodiment of FIG. 1G. The hemostasis valve system 100' can include a hemostasis valve 110' and another medical device such as first medical device 105'. The hemostasis valve 110' can be releasably coupleable to the first medical device 105'. In various embodiments, the first medical device 105' may be a valved medical device (e.g., a traditional hemostasis valve, a valved sheath introducer, etc.). Other suitable first medical devices 105' are also within the scope of this disclosure. In some embodiments, the hemostasis valve 110' may include a hemostasis valve lumen 111' that may extend between the proximal end portion 116' and a distal end portion 118' of the hemostasis valve 110'.

In certain embodiments, the hemostasis valve 110' is independent of the hemostasis valve system 100'. For example, the hemostasis valve 110' may be provided and/or used without the first medical device 105' or any other component of the hemostasis valve system 100' as provided herein. Furthermore, the hemostasis valve 110' may be configured for universal adaption. That is, the hemostasis valve 110' may be coupleable to a first medical device 105' of any suitable size. For example, the first medical device 105' may be an introducer having a size between about 4 French and about 8.5 French, and the hemostasis valve 110' may be coupleable to the introducer. In some embodiments, the hemostasis valve as disclosed herein may be an integral component of a medical device. The present disclosure contemplates various medical devices that may be integral with the hemostasis valve, such as sheaths, catheters, tubes, and so forth. For example, hemostasis valves within the scope of this disclosure may be removably or fixedly coupled to the hub of an introducer sheath.

In some embodiments, the hemostasis valve 110' can include a body 120' and a valve member 130'. The valve member 130', or at least a portion of the valve member 130', may be formed from a resilient material or a stretchable material. For example, the valve member 130' may be formed from an elastomeric material. The valve member 130' can be coupled to the body 120' at a position at or adjacent to the proximal end portion 116' of the body 120'.

In certain embodiments, the hemostasis valve 110' can further include a cap 140'. The cap 140' may be coupled to the body 120' such that at least a portion of the valve member 130' is disposed between at least a portion of the body 120' and at least a portion of the cap 140'. For example, the cap 140' may secure the valve member 130' to the body 120'. The cap 140' may be releasably coupleable to the body 120'. For example, a practitioner may desire to remove the cap 140' to access the valve member 130'. In various embodiments, the practitioner may desire to access the valve member 130', for example, to replace the valve member 130', to clean the valve member 130', etc. In various embodiments, the cap 140' may provide protection to at least a portion of the valve member 130'. For example, the cap 140' may be formed from a rigid material and the cap 140' may limit or prevent at least a portion of the valve member 130' from being compromised or damaged (e.g., upon contact with a surface, a body part, another medical device, etc.). In various other embodiments, the hemostasis valve 110' may lack the cap 140'. The valve member 130' may comprise a swabable or cleanable surface. The valve member 130' surface may be accessible for swabbing or cleaning with or without the cap 140' attached to the valve member 130'.

In some embodiments, the hemostasis valve 110', or at least a portion of the hemostasis valve 110', may be formed from a clear or transparent material. Accordingly, a color of a portion (e.g., an end) of an introducer that is coupled to the hemostasis valve 110' may be visible (e.g., to a practitioner) through at least a portion of the hemostasis valve 110'. In certain embodiments, the color of the end of the introducer may correspond to the size (e.g., the French size) of the introducer.

In various embodiments, the hemostasis valve 110', or at least a portion of the hemostasis valve 110', may include one or more indicia to indicate the size of the hemostasis valve 110' to a user. The indicium may be a color. For example, the hemostasis valve 110', or at least a portion of the hemostasis valve 110', may be blue and the blue color may correspond to a size of 8.5 French, which may indicate to a user that two or more elongate medical devices may be disposed through the hemostasis valve 110' that add up to a total of 8 French (e.g., two 4 French catheters, a 2 French catheter and a 6 French catheter, etc.). Other suitable colors and corresponding sizes are also within the scope of this disclosure. In some embodiments, the hemostasis valve 110' may be a neutral color, including clear or white.

In some embodiments, the valve member 130' may include a first sealable opening 132a' disposed through a first portion of the valve member 130'. As shown, the valve member 130' may also include a second sealable opening 132b' disposed through a second portion of the valve member 130'. The first and second portions of the valve member 130' may be adjacent to each other (e.g., as shown in FIGS. 1G and 1I), or the first and second portions of the valve member 130' may be spaced apart from each other. Other suitable dispositions of the first and second portions of the valve member 130' are also within the scope of this disclosure. In other embodiments, the hemostasis valve 110' may comprise multiple valve members that are separate and distinct from the other valve members. In some embodiments, multiple valve members may be coupled to a hub that is disposed at or adjacent to the proximal end portion of the hemostasis valve. The multiple valve members may be adjacent to each other or the multiple valve members may be spaced apart from each other. The valve members may be fabricated from a elastomeric material.

In some circumstances, a practitioner may desire to access and/or treat two branches of a vessel (e.g., simultaneously or sequentially). As further discussed herein, a hemostasis valve having two or more sealable openings, as disclosed herein, may aid in such access and/or treatment. Furthermore, the first sealable opening 132a' may include a first slit 134a" disposed through at least a portion of the first sealable opening 132a' and/or along at least a portion of the diameter of the first sealable opening 132a'. The first sealable opening 132a' may also include a second slit 134b", wherein the second slit 134b" may intersect at least a portion of the first slit 134a". Likewise, the second sealable opening 132b' may include the first slit 134a'" disposed through at least a portion of the second sealable opening 132b' and/or along at least a portion of the diameter of the second sealable opening 132b'. The second sealable opening 132b' may also include a second slit 134b'", wherein the second slit 134b'" may intersect at least a portion of the first slit 134a'". As depicted, the first slits 134a", 134a'" may be disposed substantially perpendicular to the second slits 134b", 134b'". The first slit 134a" may be continuous with the first slit 134a'". Stated another way, the first slit 134a" can be integral with the first slit 134a'". In some other embodiments, the first slit 134a" and the first slit 134a'" may be separate or distinct slits. In certain embodiments, the valve member 130' may include a third sealable opening, a fourth sealable opening, a fifth sealable opening, a sixth sealable opening, a seventh sealable opening, an eighth sealable opening, or more sealable openings.

The sealable openings (e.g., the first sealable opening 132a' and the second sealable opening 132b') may be configured such that an elongate medical device (e.g., a guidewire, a stylet, a catheter, etc.) may be disposed through at least a portion of the slits of the sealable opening, and the sealable opening and/or the slits may form a seal (e.g., a hemostatic seal) around the elongate medical device. In some embodiments, the sealable openings, or at least a portion of each of the sealable openings, may be formed from a resilient or stretchable material such that the sealable opening and/or the slits of the sealable opening may form a seal (e.g., around an outside surface of an elongate medical device). The sealable openings may also be configured such that the sealable openings are substantially sealed when no object (e.g., an elongate medical device) is disposed through the sealable openings. An elongate medical device may be disposed through the first sealable opening 132a' and then the elongate medical device may be transitioned along at least a portion of the first slits 134a", 134a'" (e.g., when the first slits 134a", 134a'" are integral) such that the elongate medical device is disposed through the second sealable opening 132b', or vice versa.

In various embodiments, the first sealable opening 132a' and/or the second sealable opening 132b' may include one or more indicia disposed on the valve member 130' to designate at least one sealable opening 132a'. 132b'. The indicia may help a practitioner identify the sealable openings 132a', 132b' based on their indicia and, in some instances, correlate each sealable opening with an elongate medical device. The indicia may be located directly on the sealable opening, above the sealable openings on the valve member 130', or to the side of the sealable opening on the valve member 130', to designate at least one sealable opening. Indicia, for example, may include categories such as numbered indicia, tactile indicia, colored indicia, shaped indicia, and the like.

In some therapies or procedures a practitioner may use two different elongate medical devices disposed through a hemostasis valve system (such as hemostasis valve system 100' of FIG. 1) as disclosed here. For example, a elongate medical device may be disposed within each sealable opening 132', 132b'. The indicia that correlate to each sealable opening may help the practitioner identify which elongate medical device is associated with each sealable opening during a medical procedure. This association between the indicia of each sealable opening and the elongate medical devices may help avoid confusion between elongate medical devices during the medical procedure.

For example, FIG. 1G illustrates an embodiment of a tactile indicium for designating sealable openings. The first sealable opening 132a' has a first tactile indicium 136a', a single protruding circle or bump, that protrudes from the valve member 130' adjacent to the first sealable opening 132a'. The second sealable opening 132b' has a second tactile indicia 136b', two protruding circles or bumps, that protrude from the valve member 130' adjacent to the second sealable opening 132b'. Indicia may include shapes, numbers, symbols, and the like that may protrude from the valve member 130' or may be depressed in the valve member 130'.

FIG. 1I is an end view of a proximal end portion 116' of the hemostasis valve system 100', with the variation that FIG. 1I illustrates alternate indicia as compared to the embodiment of FIG. 1G. In other words, FIG. 1I may be understood as an end view of the system 100' of FIG. 1G, with the indicia of FIG. 1G replaced by the alternate indicia of FIG. 1I. Thus, FIG. 1I illustrates an alternative indicia, numbered indicia, for designating sealable openings. The first sealable opening 132a' may have a numbered indicium 136a''', the number "1", to designate the first sealable opening 132a' as the first sealable opening 132a'. The second sealable opening 132b' may have a corresponding numbered indicium 136b''', the number "2", to designate the second sealable opening 132b' as the second sealable opening 132b'. Additional numbered indicia may include letters, roman numerals, and the like.

In some embodiments, the sealable openings may include colored indicia for designating the sealable openings. For example, the first sealable opening 132a' may be one color and the second sealable opening 132b' may be a different color, for example, red and green. In some embodiments, the sealable opening may include colored shapes for designating the sealable opening. As illustrated in FIG. 1I, an outer edge 137a' of the first sealable opening 132a' may be one color and an outer edge 137b' of the second sealable opening 132b' may be a different color. In some embodiments, one of the sealable opening may include a colored circle that surrounds the sealable opening and the other sealable opening may include two colored circles that surround the sealable opening with one circle having a greater diameter than the other circle.

In some embodiments, tactile, numbered, colored, and shaped indicia may overlap in the sense that a single indicia may comprise various categories. For example, a first indicia for the first sealable opening 132a' may include a numbered indicia that has one color and protrudes from the valve member 130' and a second indicia for the second sealable opening 132b' may include a different number and a different color and protrudes from the valve member 130'. In some embodiments, each sealable opening may include multiple different indicia that do not overlap with each other and are separate from the other indicia.

With continued reference to FIGS. 1G-1I, the hemostasis valve 110 may further include a sidearm 112'. The sidearm 112' may include a sidearm lumen 114', the sidearm lumen 114' extending through at least a portion of the sidearm 112'. In some embodiments, the sidearm lumen 114' may be in fluid communication with a lumen or a hemostasis valve lumen 111' of the hemostasis valve 110. Accordingly, a practitioner may dispose or introduce a fluid through the sidearm lumen 114' to flush and/or clean at least a portion of the hemostasis valve lumen 111'.

The first medical device 105' may also include a sidearm 109'. The sidearm 109' may include a sidearm lumen 104', the sidearm lumen 104' extending through at least a portion of the sidearm 109'. In some embodiments, the sidearm lumen 104' may be in fluid communication with a lumen or a first medical device lumen of the first medical device 105'. Accordingly, a practitioner may dispose or introduce a fluid through the sidearm lumen 104' to flush and/or clean at least a portion of the first medical device lumen 103'. The sidearm 112' may rotate independent of the sidearm 109', for example, when the hemostasis valve 110' is coupled to the first medical device 105'. Furthermore, the hemostasis valve 110' may be configured such that upon coupling of the hemostasis valve 110' to the first medical device 105', the sidearm lumen 104' is not blocked by a portion of the hemostasis valve 110'. For example, fluid communication through the sidearm lumen 104' may be substantially maintained upon coupling of the hemostasis valve 110' to the first medical device 105'. In various embodiments, each of the sidearm lumens 104', 114' may be in fluid communication with each of the first medical device lumen 103' and the hemostasis valve lumen 111' (e.g., when the first medical device 105' is coupled to the hemostasis valve 110').

In some embodiments, the axis of the sidearm 109' and the axis of the sidearm 112' are aligned with each other. In addition, the sidearms 109', 112' may be aligned with the sealable openings 132a', 132b' as illustrated in FIGS. 1G and 1I. As discussed above, in some embodiments, sidearm 109' may rotate independent of sidearm 112', thus the practitioner may be able to align both sidearms 109', 112' with the sealable openings 132a', 132b', or the practitioner may simply align only one of the sidearms 109', 112' with the sealable openings 132a', 132b'. Alternatively, in other embodiments, one or both sidearms 109', 112' may be in a fixed relationship in which the one or both sidearms 109', 112' are aligned with the sealable openings 132a', 132b' and the sidearms 109', 112' are unable to rotate.

In some embodiments, a valve member 130' with multiple sealable openings is part of an introducer with a lumen. The sealable openings may be in communication with the lumen of the introducer. The introducer may have a sidearm also in communication with the lumen of the introducer.

The alignment between the sidearms 109', 112' and sealable openings 132a', 132b' may enable a practitioner to place the hemostasis valve system 100' and the sidearms 109', 112' on a flat surface and have the sealable openings 132a', 132b' horizontally adjacent to allow the practitioner to insert elongated medical devices through the sealable openings. The horizontal orientation of the sidearms 109', 112' and the sealable openings 132a', 132b' may provide ease of access for the practitioner to engage with the elongated medical devices inserted into the sealable openings and improve organization of the multiple elongated medical devices inserted into the sealable openings 132a', 132b'. For example, the hemostasis valve 110' may be placed on a flat surface, such as a tray next to a patient, or even on top of the patient. When so placed, the design of the hemostasis valve 110', including the orientation of the side arms 109', 112' with respect to the sealable openings 132a', 132b', may thus result in a horizontal orientation for the sealable openings 132a', 132b'. The horizontal orientation of the sealable openings 132a', 132b' may insertion and manipulation of different elongate medical devices into each sealable opening 132a', 132b' by a practitioner. The horizontal orientation may reduce instances wherein the elongate medical devices interact with each other, may provide an open and/or ergonomic grasping area for the elongate medical devices, and may facilitate organization of the elongate medical devices.

The hemostasis valve 110' may also include a coupling member (not shown) disposed, for example, at or adjacent to the distal end portion 118' of the hemostasis valve 110'. The coupling member may be configured to couple, or releasably couple, the hemostasis valve 110' to the first medical device 105'. In certain embodiments, the coupling member may be configured to form a snap fit between the hemostasis valve 110' and the first medical device 105'. For example, the coupling member may be a barb fit, a press fit, a luer fitting, and the like. In certain other embodiments, the coupling member may be configured to threadably couple the hemostasis valve 110' and the first medical device 105' to each other (e.g., the coupling member may include one or more threads). Other suitable coupling mechanisms are also within the scope of this disclosure.

Figure 2:
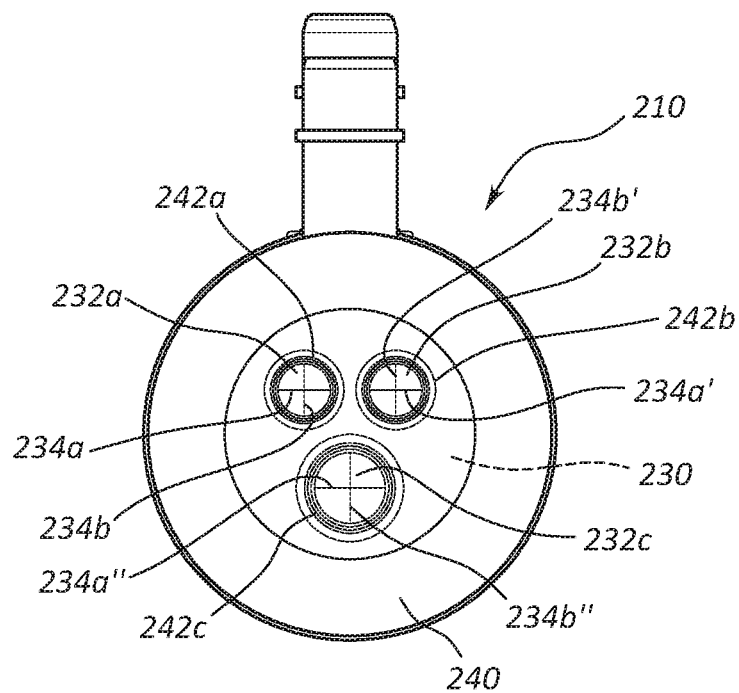
FIG. 2 is an end view of a proximal end portion of a hemostasis valve.

FIG. 2 illustrates a hemostasis valve 210 that can, in certain respects, resemble components of the hemostasis valve 110 described in connection with FIGS. 1A-1E. It will be appreciated that all the illustrated embodiments may have analogous features. Accordingly, like features are designated with like reference numerals, with the leading digits incremented to "2." For instance, the cap is designated as "140" in FIGS. 1A-1E, and an analogous cap is designated as "240" in FIG. 2. Relevant disclosure set forth above regarding similarly identified features thus may not be repeated hereafter. Moreover, specific features of the hemostasis valve 110 and related components shown in FIGS. 1A-1E may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the hemostasis valve 210 of FIG. 2. Any suitable combination of the features, and variations of the same, described with respect to the hemostasis valve 110 and components illustrated in FIGS. 1A-1E can be employed with the hemostasis valve 210 and components of FIG. 2, and vice versa. This pattern of disclosure applies equally to further embodiments depicted in subsequent figures and described hereafter.

FIG. 2 is an end view of a proximal end of a hemostasis valve 210. The hemostasis valve 210 can include a valve member 230. As depicted, the valve member 230 may include a first sealable opening 232a disposed through a first portion of the valve member 230. The valve member 230 may also include a second sealable opening 232b disposed through a second portion of the valve member 230. A first slit 234a and a second slit 234b may be disposed through at least a portion of the first sealable opening 232a, and a first slit 234a' and a second slit 234b' may be disposed through at least a portion of the second sealable opening 232b. As depicted, the first sealable opening 232a may be substantially the same size as the second sealable opening 232b. In some other embodiments, the first sealable opening 232a may be larger than the second sealable opening 232b, or vice versa.

The valve member 230 may also include a third sealable opening 232c disposed through a third portion of the valve member 230. Furthermore, a first slit 234a" and a second slit 234b" may be disposed through at least a portion of the third sealable opening 232c. As depicted, the third sealable opening 232c may be larger than each of the first sealable opening 232a and the second sealable opening 232b. In various embodiments, a practitioner may displace a first guidewire through the first sealable opening 232a and a second guidewire through the second sealable opening 232b. The practitioner may also displace an elongate medical device having a larger profile than either of the first or second guidewire through the third sealable opening 232c (e.g., such as a balloon catheter).

In some embodiments, the hemostasis valve 210 may include one or more exchange slits (not shown) and may lack a cap. For example, the exchange slit can be disposed through a portion of the valve member 230 and extend between the first sealable opening 232a and the third sealable opening 232c. As such, the practitioner may dispose the first guidewire through the first sealable opening 232a, through the hemostasis valve 210, and then into at least a portion of a vessel of a patient. The practitioner may then displace the first guidewire from the first sealable opening 232a to the third sealable opening 232c via the exchange slit. Upon displacement of the first guidewire to the third sealable opening 232c, the practitioner may then dispose an elongate medical device such as a balloon catheter over and along the first guidewire and through the third sealable opening 232c of the hemostasis valve 210. The hemostasis valve 210 may include one, two, three, or more exchange slits. For example, a second exchange slit may be disposed between the second sealable opening 232b and the third sealable opening 232c.

Other relative sizes of the each of the first, second, and third sealable openings 232a, 232b, 232c are also within the scope of this disclosure. For example, in some other embodiments, each of the first, second, and third sealable openings 232a, 232b, 232c may be a different size (e.g., the first sealable opening 232a may be a first size, the second sealable opening 232b may be a second size, and the third sealable opening 232c may be a third size).

The sealable openings (e.g., the first sealable opening 232a, the second sealable opening 232b, the third sealable opening 232c) may be configured such that an elongate medical device (e.g., a guidewire, a stylet, a catheter, etc.) may be disposed through at least a portion of the slits of the sealable opening and the sealable opening and/or the slits may form a seal (e.g., a hemostatic seal) around the elongate medical device.

In some embodiments, a first balloon catheter may be disposed through the first sealable opening 232a and a second balloon catheter may be disposed through the second sealable opening 232b. Furthermore, a contrast agent (e.g., for an angiogram) may be introduced through the third sealable opening 232c (e.g., via a catheter). For example, the first and second sealable openings 232a, 232b may be configured to seal around at least a portion of 12 French first and second balloon catheters and the third sealable opening 232c may be configured to seal around at least a portion of a 14 French contrast agent catheter.

The hemostasis valve 210 may also include the cap 240. The cap 240 may be coupleable to a proximal end portion of the hemostasis valve 210 such that at least a portion of the valve member 230 is disposed between the cap 240 and a body of the hemostasis valve 210. As stated above, in some other embodiments, the hemostasis valve 210 may lack a cap. The cap 240 can include a first cap opening 242a and a second cap opening 242b. The first cap opening 242a may be disposed through the cap 240 such that upon coupling of the cap 240 to the hemostasis valve 210, the first cap opening 242a is in substantial alignment with the first sealable opening 232a. The second cap opening 242b may be disposed through the cap 240 such that upon coupling of the cap 240 to the hemostasis valve 210, the second cap opening 242b is in substantial alignment with the second sealable opening 232b. The cap 240 may also include a third cap opening 242c. The third cap opening 242c may be disposed through the cap 240 such that upon coupling of the cap 240 to the hemostasis valve 210, the third cap opening 242c is in substantial alignment with the third sealable opening 232c.

Figure 3:
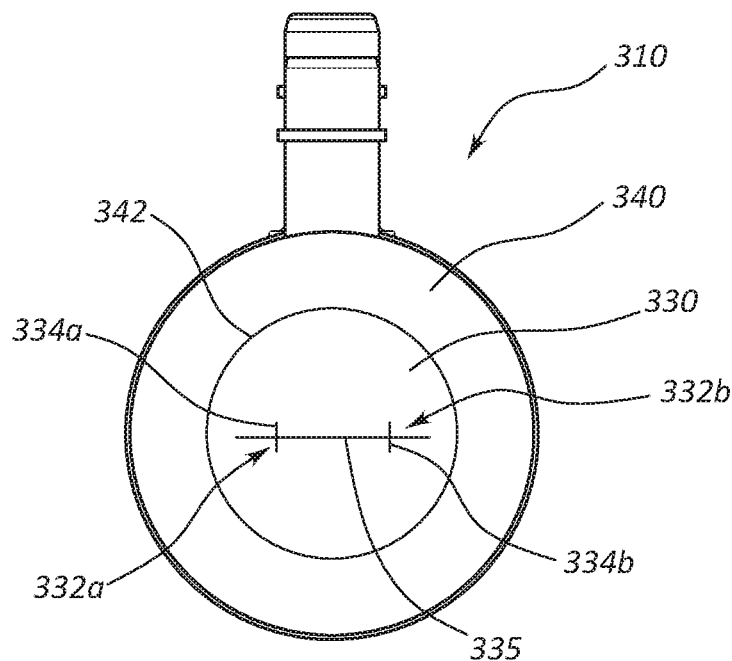
FIG. 3 is an end view of a proximal end portion of another embodiment of a hemostasis valve.

FIG. 3 is an end view of a proximal end of a hemostasis valve 310. The hemostasis valve 310 can include a valve member 330. As depicted, the valve member 330 may include a first sealable opening 332a disposed through a first portion of the valve member 330 and a second sealable opening 332b disposed through a second portion of the valve member 330. A first slit 334a may be disposed through at least a portion of the first sealable opening 332a, and a second slit 334b may be disposed through at least a portion of the second sealable opening 332b. Furthermore, an elongate slit 335 may be disposed through a portion of the valve member 330. The first sealable opening 332a and the second sealable opening 332b may be coupled via the elongate slit 335. In such a configuration, a first elongate medical device may be disposed through the first sealable opening 332a and then displaced from the first sealable opening 332a to the second sealable opening 332b via the elongate slit 335. Likewise, a second elongate medical device may be disposed through the second sealable opening 332b and then displaced from the second sealable opening 332b to the first sealable opening 332a via the elongate slit 335.

The hemostasis valve 310 may also include a cap 340. The cap 340 can include a cap opening 342. The cap opening 342 may be disposed through the cap 340 such that upon coupling of the cap 340 to the hemostasis valve 310, the cap opening 342 is disposed around each of the first and second sealable openings 332a, 332b and/or provides access (e.g., to a practitioner) to each of the first and second sealable openings 332a, 332b.

Figure 4A:
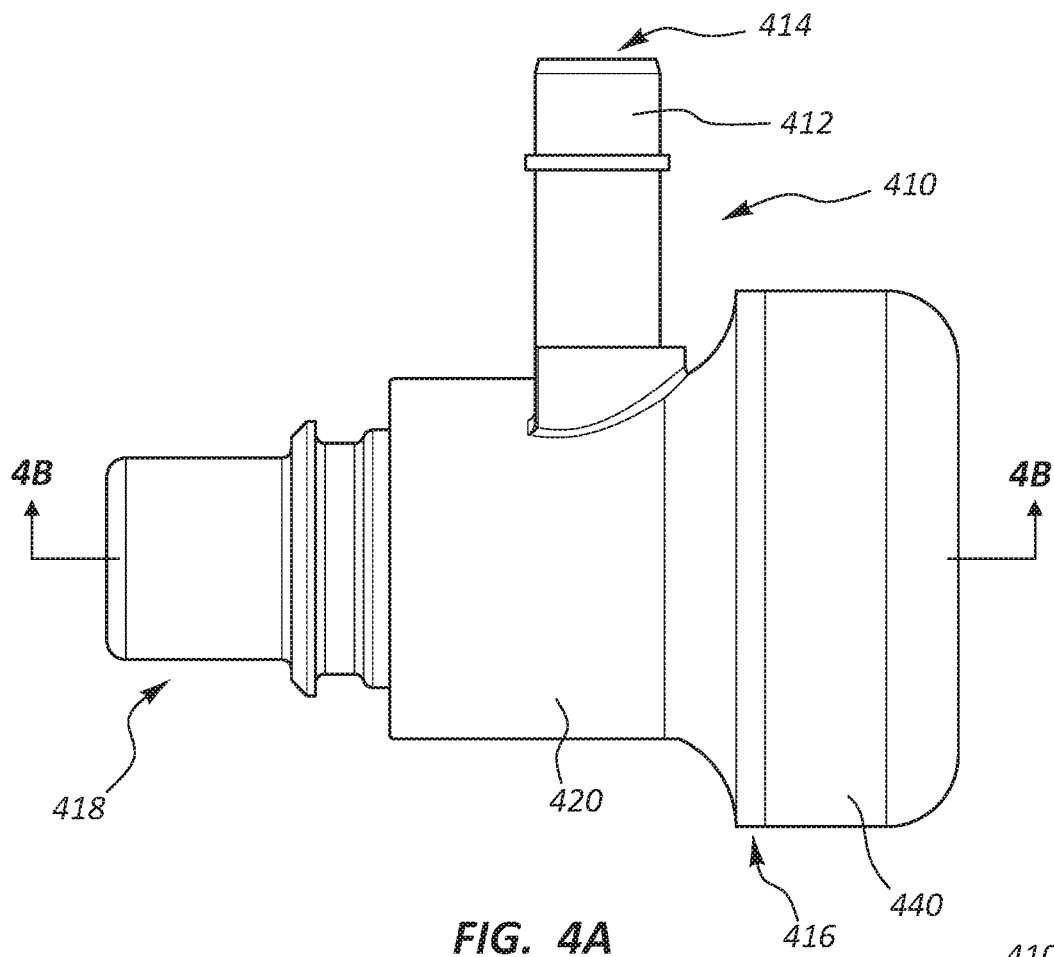
FIG. 4A is a side view of another embodiment of a hemostasis valve.
Figure 4B:
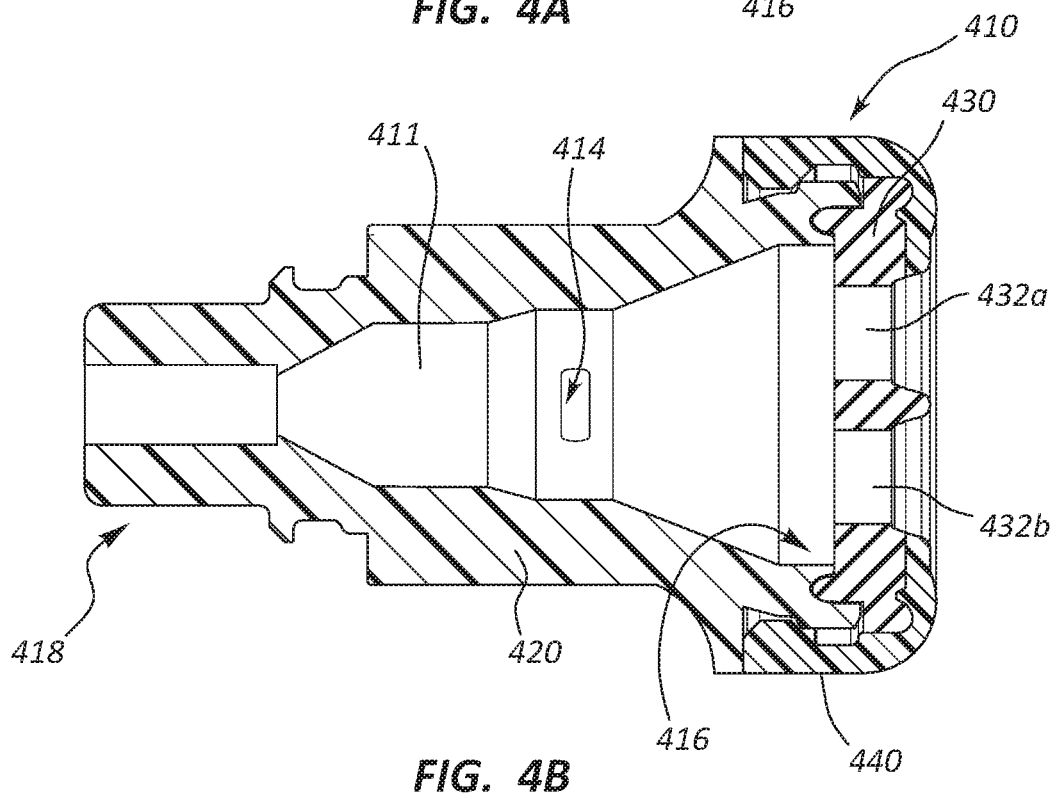
FIG. 4B is a cross-sectional view of the hemostasis valve of FIG. 4A taken through line 4B-4B.
Figure 4C:
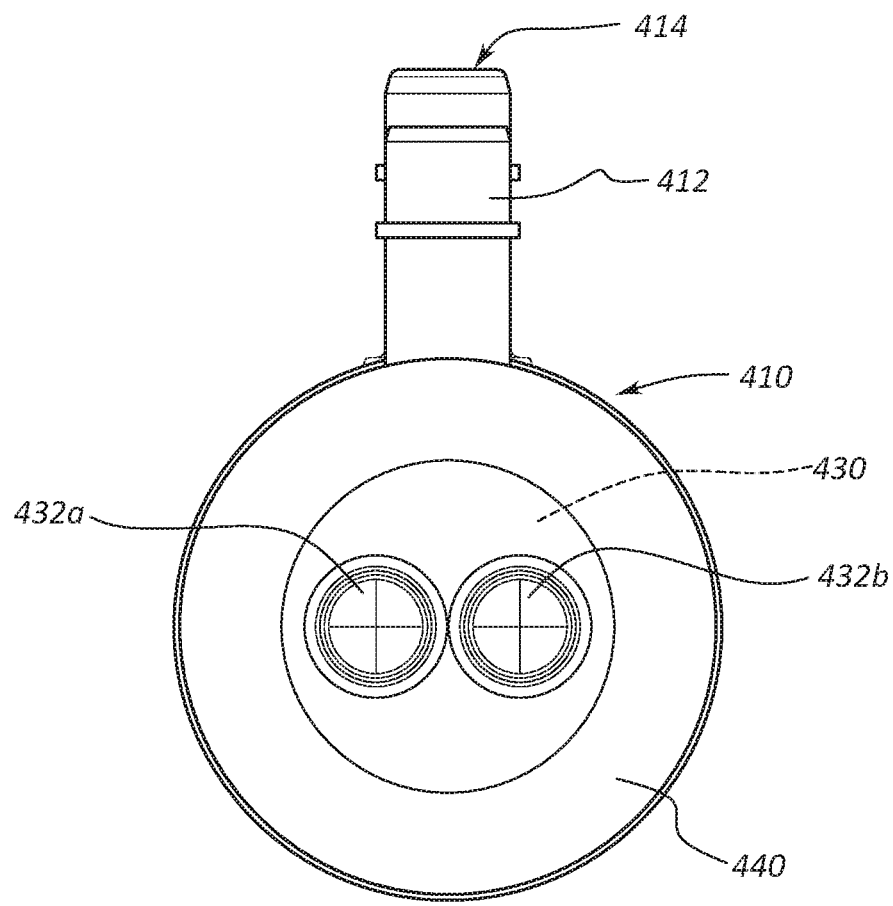
FIG. 4C is an end view of a proximal end portion of the hemostasis valve of FIG. 4A.

FIG. 4A is a side view of a hemostasis valve 410, FIG. 4B is a cross-sectional view of the hemostasis valve 410 through line 4B-4B of FIG. 4A, and FIG. 4C is an end view of a proximal end of the hemostasis valve 410. The hemostasis valve 410 can include a body 420 extending between a proximal end portion 416 and a distal end portion 418. The hemostasis valve 410 can also include a valve member 430, wherein the valve member 430 may be coupled to the body 420 at a position at or adjacent the proximal end portion 416. The hemostasis valve 410 can further include a cap 440, wherein the cap 440 may be coupled to the body 420 such that at least a portion of the valve member 430 is disposed between at least a portion of the body 420 and at least a portion of the cap 440. In some embodiments, the hemostasis valve 410 may lack a cap.

The valve member 430 can include a first sealable opening 432a disposed through a first portion of the valve member 430 and a second sealable opening 432b disposed through a second portion of the valve member 430. The hemostasis valve 410 can further include a sidearm 412. The sidearm 412 can include a sidearm lumen 414, wherein the sidearm lumen 414 can extend through at least a portion of the sidearm 412. As depicted, the sidearm lumen 414 may be in fluid communication with at least a portion of a hemostasis valve lumen 411 of the hemostasis valve 410. Furthermore, the hemostasis valve lumen 411 can extend through at least a portion of the hemostasis valve 410. As illustrated, the hemostasis valve lumen 411 extends between the proximal end portion 416 and the distal end portion 418 of the hemostasis valve 410. As discussed above regarding the hemostasis valve lumen 111, the shape of the hemostasis valve lumen 411 can aid in the displacement of an elongate medical device through the hemostasis valve 410.

Figure 4D:
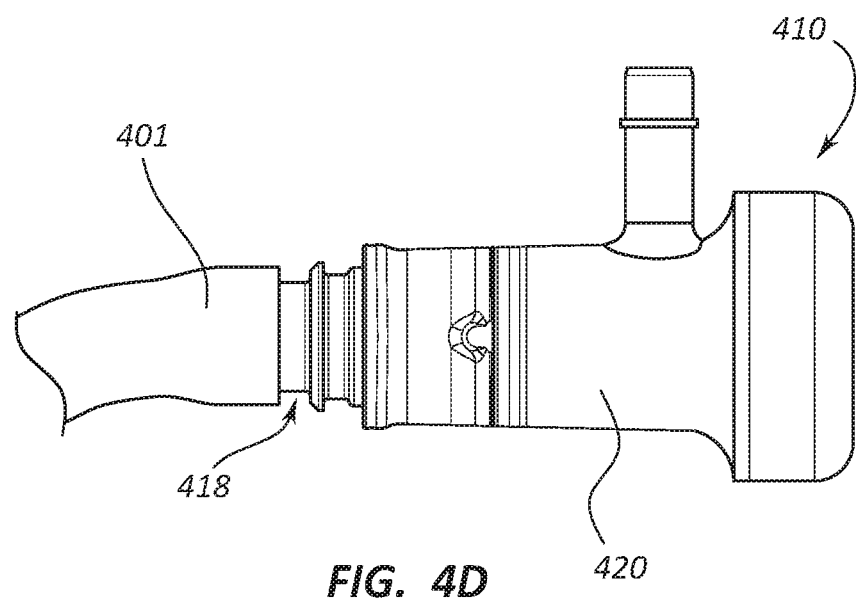
FIG. 4D is a side view of the hemostasis valve of FIG. 4A coupled to an introducer sheath.

The distal end portion 418 of the hemostasis valve 410 may be configured such that the hemostasis valve 410 can be coupled to another medical device. For example, a coupling mechanism may be coupled to or disposed at or adjacent the distal end portion 418 (e.g., a luer connector, a snap fit mechanism, a plurality of threads). In some embodiments, another medical device may extend distally from the distal end portion 418 of the hemostasis valve 410. For example, a sheath introducer may be integral with the hemostasis valve 410 and the sheath introducer may extend distally from the distal end portion 418. Other suitable medical devices may also be coupled to or integral with the hemostasis valve 410 (e.g., a catheter, medical tubing, etc.). FIG. 4D is a side view of the hemostasis valve 410 coupled to an introducer sheath 401 adjacent the distal end portion 418 of the body 420.

Analogous to the introducer sheath 401 of FIG. 4D, any of the hemostasis valves described herein may be coupled to a variety of elongate medical devices, including introducer sheaths, catheters, conduits, and so forth. As noted above, in some instances the hemostasis valve may snap onto the hub of an elongate device, including hubs that include an existing hemostasis valve. In other embodiments, the hemostasis valves described herein may be configured to attach to an elongate medical instrument via a luer lock. For instances, a hemostasis valve within the scope of this disclosure may comprise a luer lock at the distal end portion 418 which may be configured to couple to a catheter; in some embodiments the catheter may be a standard catheter with a luer fitting on its proximal end. Similarly, hemostasis valves described herein may be coupled to a variety of devices through use of a variety of connectors, including snap fits, luer fittings, barb fittings, adhesives, and so forth.

Figure 5:
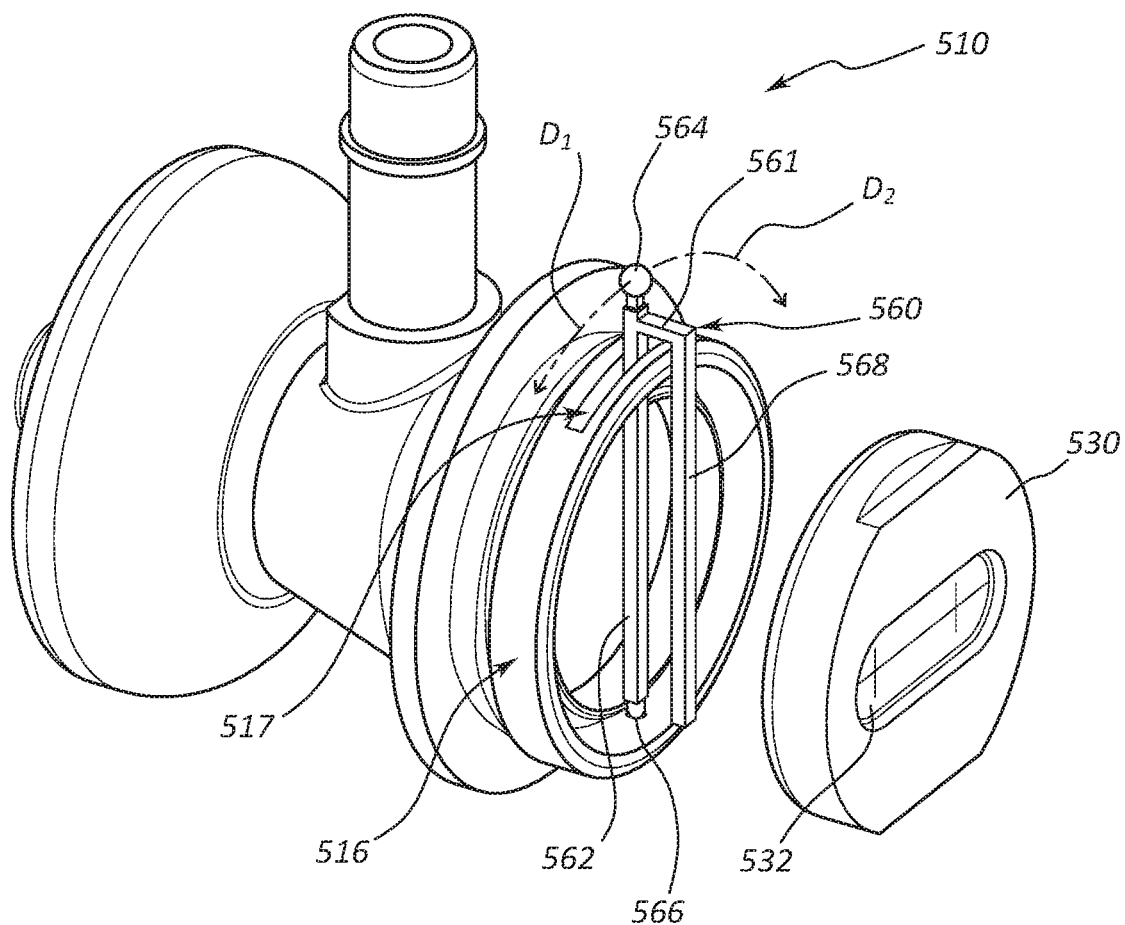
FIG. 5 is an exploded view of another embodiment of a hemostasis valve.

FIG. 5 is an exploded view of a hemostasis valve 510 including a valve dividing member 560. As illustrated, the valve dividing member 560 can include a first elongate portion 562 that extends between an actuator 564 and a hinge portion 566. Furthermore, the first elongate portion 562 can extend through a slot 517, wherein the slot 517 is disposed through a proximal end portion 516 of the hemostasis valve 510. The valve dividing member 560 can further include a second elongate portion 568, wherein the second elongate portion 568 is coupled to the first elongate portion 562 and/or the actuator 564 via a transverse portion 561.

Upon coupling of the hemostasis valve 510 to a valve member 530, the first elongate portion 562 and the second elongate portion 568 may be configured to couple, engage with, and/or interact with the valve member 530. The first elongate portion 562 and the second elongate portion 568 may be configured as a divider displaceable along a sealable opening 532 of the valve member 530. The divider may allow a practitioner to divide the sealable opening 532 into a first side and a second side, for example to separate two guidewires positioned in different points of a patient's anatomy. Displacement of the valve dividing member 560 in one direction may increase the available space to advance a larger therapy (such as a balloon) over one guidewire. At the conclusion of the initial therapy, the valve dividing member 560 could be displaced in the other direction to provide more space for treatment via a wire on the other side of the valve dividing member 560. This embodiment may allow a practitioner to separate two guidewires and accommodate larger therapies when needed, while minimizing the overall size of the hemostasis valve 510.

The first elongate portion 562 and the second elongate portion 568 may provide structure and support above and below the valve member 530 such that a practitioner may displace the first elongate portion 562 and the second elongate portion 568 to change the effective length of the sealable opening 532 on other side of the first elongate portion 562 and the second elongate portion 568. This support structure may allow the sealable opening 532 to remain sealed on a guidewire on one side of the valve dividing member 560 while a large therapy such as a balloon is inserted through the sealable opening 532 on the other side of the valve dividing member 560. The support structure may facilitate simultaneous sealing of the sealable opening 532 on both the balloon on one side and a guidewire on the other side of the valve dividing member 560.

The valve dividing member 560 may be configured to be displaceable between at least a resting position, a first lateral position, and a second lateral position. The resting position may correlate to a central position when the valve dividing member 560 is disposed in a middle portion of the valve member 530 (e.g., as depicted in FIG. 5). Displacement of the valve dividing member 560 (e.g., via the actuator 564) in a first direction as indicated by the arrow $D_1$ may displace the first elongate portion 562 and the second elongate portion 568 in the first direction (i.e., to the first lateral position). In the first lateral position, the sealable opening 532 has a longer effective or usable length on the side of the first elongate portion 562 and the second elongate portion 568 associated with the second direction (indicated by arrow $D_2$). Thus, in this position a practitioner may be able to advance larger therapies (such as a balloon) through the sealable opening 532 on the side of the valve dividing member 560 associated with the second direction. Again, the sealable opening 532 may simultaneously seal against a guidewire on the first side of the valve dividing member 560 and a larger device on the second side of the valve dividing member 560.

Likewise, displacement of valve dividing member 560 in a second direction as indicated by the arrow $D_2$ may displace at least a portion of the first elongate portion 562 and the second elongate portion 568 in the second direction (i.e., to the second lateral position). This displacement may provide a greater effective length of the sealable opening 532 on the side of the valve dividing member 560 associated with the first direction.

In some other embodiments, a first iris-like support member may provide structure and support above a valve member and/or a second iris-like support member may provide structure and support below the valve member. At least a portion of the iris-support member may be analogous to a camera aperture. The first and/or second iris-like support members may be configured to transition from a first diameter to a second diameter, wherein the first diameter is greater than the second diameter. The first and/or second iris-like support members may be disposed around a sealable opening, as provided herein, having a first slit and a second slit wherein the intersecting first and second slits form at least four leaflets in the valve member at the sealable opening.

When the first and/or second iris-like support members are in the first diameter, a first elongate medical device having a first diameter may be disposed through the sealable opening and the leaflets can form a seal around the first elongate medical device. When a second elongate medical device having a second, smaller diameter is disposed through the sealable opening, a practitioner may transition the first and/or second iris-like support members to the second smaller diameter such that the leaflets are supported (i.e., by the first and/or second iris-like support members) and can form a seal around the second elongate medical device having the second, smaller diameter.

Figure 6:
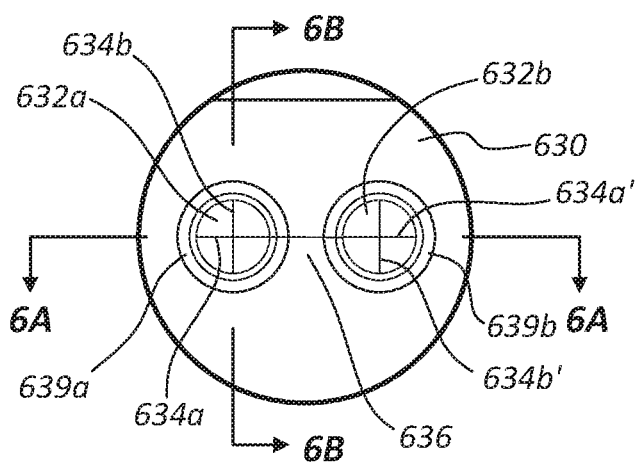
FIG. 6 is an end view of a valve member.
Figure 6A:
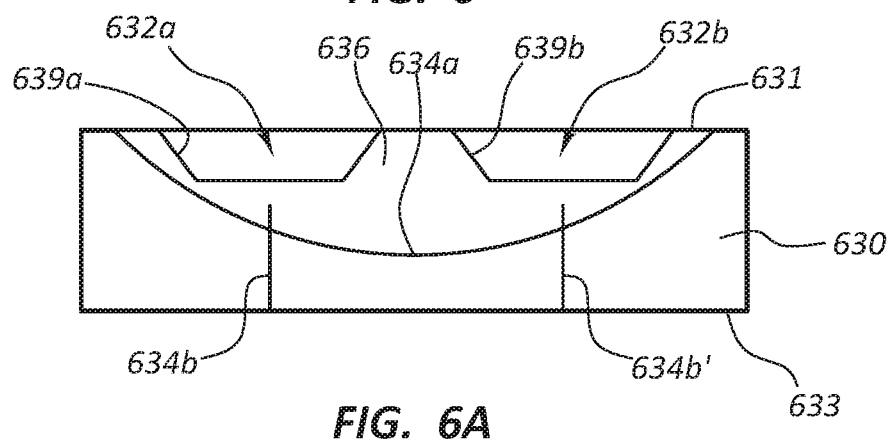
FIG. 6A is a cross-sectional view of the valve member of FIG. 6 taken through line 6A-6A.
Figure 6B:
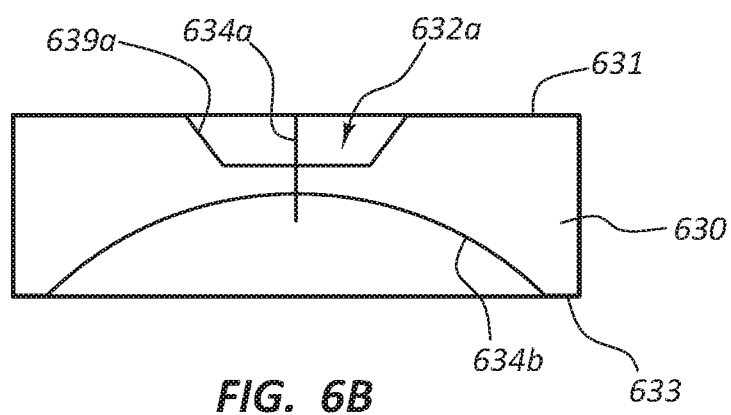
FIG. 6B is a cross-sectional view of the valve member of FIG. 6 taken through line 6B-6B.

FIG. 6 illustrates a valve member 630. FIG. 6A is a cross-sectional view of the valve member 630 taken through line 6A-6A and FIG. 6B is a cross-sectional view of the valve member 630 taken through line 6B-6B. As shown, the valve member 630 can include a first sealable opening 632a having a first slit 634a disposed through at least a portion of the first sealable opening 632a and/or along at least a portion of the diameter of the first sealable opening 632a. The first sealable opening 632a may also include a second slit 634b, wherein the second slit 634b may intersect at least a portion of the first slit 634a. Likewise, the first slit 634a may be disposed through at least a portion of a second sealable opening 632b and/or along at least a portion of the diameter of the second sealable opening 632b. The second sealable opening 632b may also include a second slit 634b', wherein the second slit 634b' may intersect at least a portion of the first slit 634a. As depicted, the first slit 634a may be disposed substantially perpendicular to the second slits 634b, 634b'.

The valve member 630 can further include a wall 636 disposed between the first sealable opening 632a and the second sealable opening 632b. As illustrated, the first slit 634a can extend through the wall 636 between each of the first and second sealable openings 632a, 632b. As discussed above, at least a portion of the wall 636 may be resilient or deformable. At least a portion of a first edge 639a surrounding the first sealable opening 632a and/or at least a portion of a second edge 639b surrounding the second sealable opening 632b may be chamfered or sloped. Such a configuration may aid in guiding an elongate medical device through the first and/or the second sealable openings 632a, 632b.

With reference to FIG. 6A, the first slit 634a may extend inward from a first surface 631 of the valve member 630 and through at least a portion of the each of the first and second sealable openings 632a, 632b. As illustrated, the first slit 634a may form a substantially arc-shaped cut or slit in at least a portion of the valve member 630. Other shapes of the first slit 634a (e.g., linear, wavy, etc.) are also within the scope of this disclosure. Furthermore, the second slits 634b, 634b' may extend inward from a second or opposite surface 633 of the valve member 630. Each of the second slits 634b, 634b' may intersect with at least a portion of the first slit 634a to form the first and second sealable openings 632a, 632b.

With reference to FIG. 6B, the first slit 634a may extend inward from the first surface 631 of the valve member 630 and through at least a portion of the first sealable opening 632a. Furthermore, the second slit 634b may extend inward from the second surface 633 of the valve member 630. The second slit 634b may intersect with at least a portion of the first slit 634a to form the first sealable opening 632a. As illustrated, the second slit 634b may form a substantially arc-shaped cut or slit in at least a portion of the valve member 630. Other shapes of the second slit 634b (e.g., linear, wavy, etc.) are also within the scope of this disclosure. The second slit 634b', which is not shown in FIG. 6B, may be configured in a similar manner to that of the second slit 634b.

Figure 7:
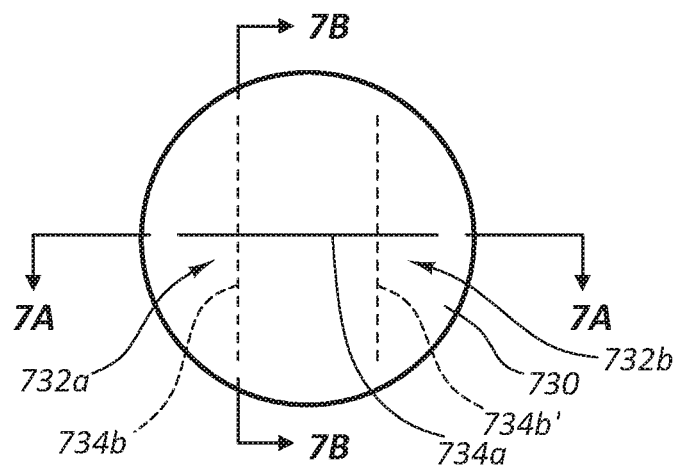
FIG. 7 is an end view of another embodiment of a valve member.
Figure 7A:
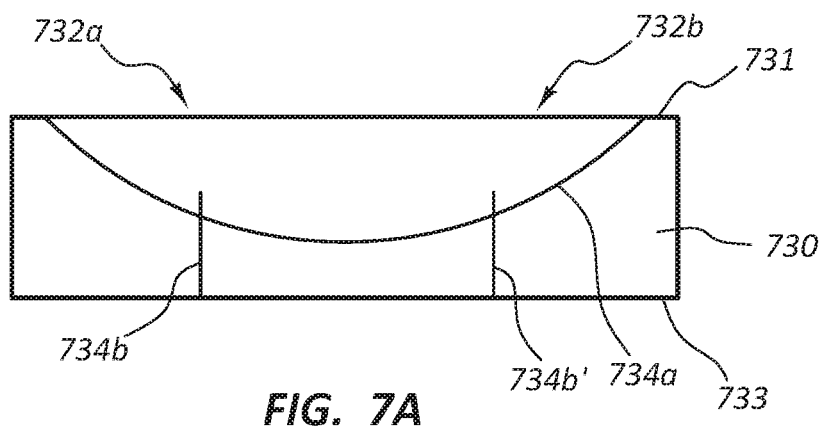
FIG. 7A is a cross-sectional view of the valve member of FIG. 7 taken through line 7A-7A.
Figure 7B:
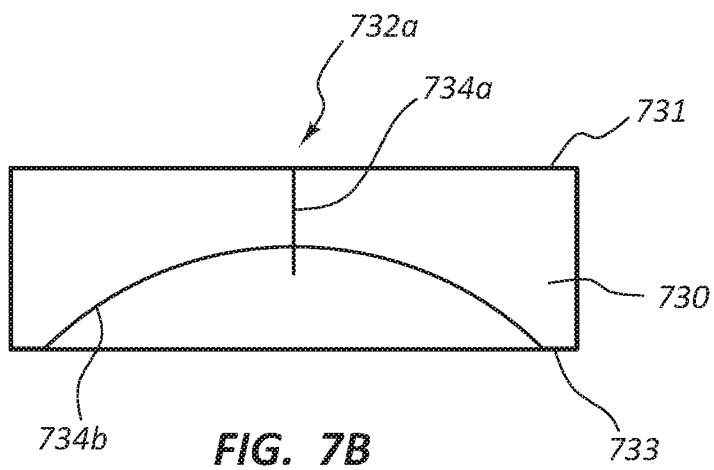
FIG. 7B is a cross-sectional view of the valve member of FIG. 7 taken through line 7B-7B.

FIG. 7 illustrates a valve member 730. FIG. 7A is a cross-sectional view of the valve member 730 taken through line 7A-7A and FIG. 7B is a cross-sectional view of the valve member 730 taken through line 7B-7B. As shown, the valve member 730 can include a first sealable opening 732a and a second sealable opening 732b. A first slit 734a can be disposed through at least a portion of the first and second sealable openings 732a, 732b. The first sealable opening 732a may also include a second slit 734b, wherein the second slit 734b may intersect at least a portion of the first slit 734a. Likewise, the second sealable opening 732b may also include a second slit 734b', wherein the second slit 734b' may intersect at least a portion of the first slit 734a. As depicted, the first slit 734a may be disposed substantially perpendicular to the second slits 734b, 734b'.

With reference to FIG. 7A, the first slit 734a may extend inward from a first surface 731 of the valve member 730 and through at least a portion of each of the first and second sealable openings 732a, 732b. As illustrated, the first slit 734a may form a substantially arc-shaped cut or slit in at least a portion of the valve member 730. Other shapes of the first slit 734a (e.g., linear, wavy, etc.) are also within the scope of this disclosure. Furthermore, the second slits 734b, 734b' may extend inward from a second or opposite surface 733 of the valve member 730. Each of the second slits 734b, 734b' may intersect with at least a portion of the first slit 734a to form the first and second sealable openings 732a, 732b.

With reference to FIG. 7B, the first slit 734a may extend inward from the first surface 731 of the valve member 730 and through at least a portion of the first sealable opening 732a. Furthermore, the second slit 734b may extend inward from the second surface 733 of the valve member 730. The second slit 734b may intersect with at least a portion of the first slit 734a to form the first sealable opening 732a. As illustrated, the second slit 734b may form a substantially arc-shaped cut or slit in at least a portion of the valve member 730. Other shapes of the second slit 734b (e.g., linear, wavy, etc.) are also within the scope of this disclosure. The second slit 734b', which is not shown in FIG. 7B, may be configured in a similar manner to the second slit 734b.

Figure 8:
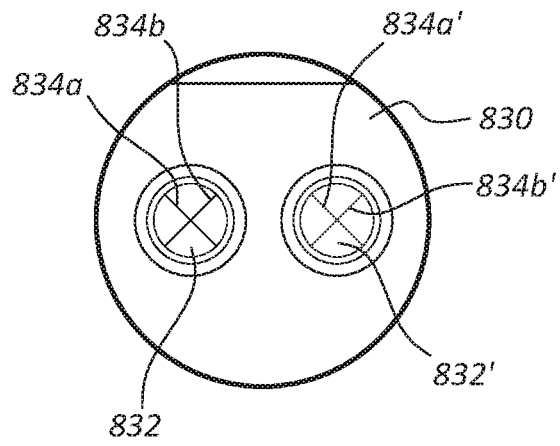
FIG. 8 is an end view of another embodiment of a valve member.

FIG. 8 illustrates a valve member 830. As shown, the valve member 830 can include a first sealable opening 832 having a first slit 834a disposed through at least a portion of the first sealable opening 832 and/or along at least a portion of the diameter of the first sealable opening 832. The first sealable opening 832 may also include a second slit 834b, wherein the second slit 834b may intersect at least a portion of the first slit 834a. Likewise, a first slit 834a' may be disposed through at least a portion of a second sealable opening 832' and/or along at least a portion of the diameter of the second sealable opening 832'. The second sealable opening 832' may also include a second slit 834b', wherein the second slit 834b' may intersect at least a portion of the first slit 834a'. As depicted, the first and second slits 834a, 834b may be disposed such that they form an X shape. The first and second slits 834a', 834b' may also be disposed such that they form an X shape. The slits forming the X shape may intersect at various angles and are not necessarily perpendicular to each other.

Figure 9:
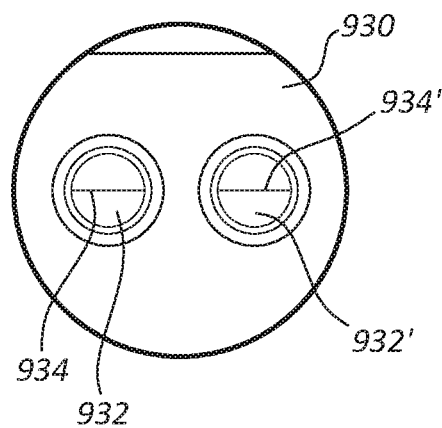
FIG. 9 is an end view of another embodiment of a valve member.

FIG. 9 illustrates a valve member 930. As shown, the valve member 930 can include a first sealable opening 932 having a single slit 934 disposed through at least a portion of the first sealable opening 932 and/or along at least a portion of the diameter of the first sealable opening 932. Likewise, a single slit 934' may be disposed through at least a portion of a second sealable opening 932' and/or along at least a portion of the diameter of the second sealable opening 932'. Any of the sealable openings and/or slits depicted in FIGS. 1A-5 may be formed in manner analogous to any of the sealable openings and/or slits depicted in FIGS. 6-9.

Figure 10:
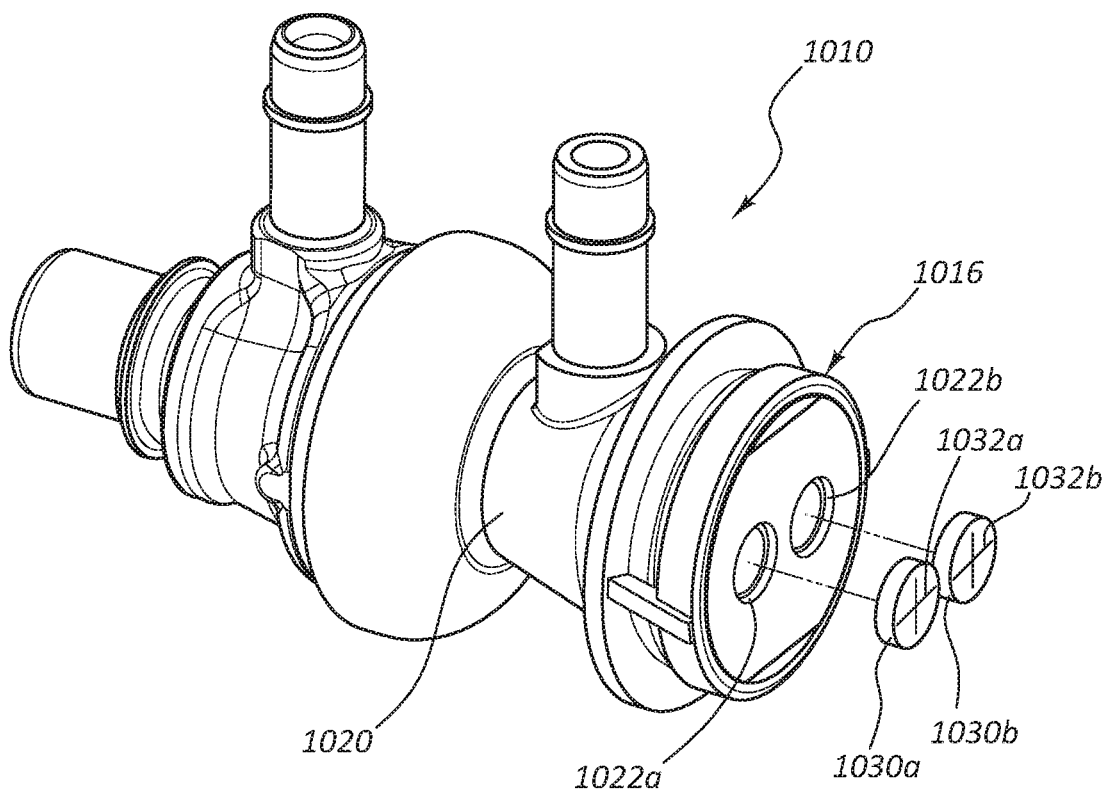
FIG. 10 is a partial exploded view of another embodiment of a hemostasis valve system.

FIG. 10 is an exploded view of a hemostasis valve 1010. The hemostasis valve 1010 can include a body 1020. The hemostasis valve 1010 can further include a first valve member 1030a and a second valve member 1030b, wherein the first and second valve members 1030a, 1030b are configured to be disposed at or adjacent a proximal end portion 1016 of the hemostasis valve 1010. Stated another way, the first and second valve members 1030a, 1030b may be coupleable to the hemostasis valve 1010 at a position at or adjacent the proximal end portion 1016 of the hemostasis valve 1010 (e.g., at a first and second valve member coupling portion 1022a, 1022b, respectively). The first and second valve member coupling portions 1022a, 1022b may be configured to limit or prevent movement (e.g., longitudinal movement) of the first and second valve members 1030a, 1030b relative to the hemostasis valve 1010 when the first and second valve members 1030a, 1030b are coupled to the hemostasis valve 1010.

As depicted, the first valve member 1030a includes a first sealable opening 1032a disposed through a first portion of the first valve member 1030a and a second sealable opening 1032b disposed through the second valve member 1030b. As discussed above, each of the first and second sealable openings 1032a, 1032b can include one or more slits disposed through at least a portion of the first and second valve members 1030a, 1030b. In some embodiments, the hemostasis valve 1010 may include three, four, five, or more valve members.

Any of the valve members depicted in FIG. 1A-9 or 11 may be formed in a manner analogous to the valve members depicted in FIG. 10. In other words, the valve member may include a single piece or member including two or more sealable openings or the valve member may include multiple pieces or members. Additionally, any of the hemostasis valves provided herein may be stand-alone hemostasis valves for use with a hemostasis valve system or the hemostasis valves may be configured such that they may retrofit a standard (e.g., off-the-shelf) hemostasis valve system.

Figure 11:
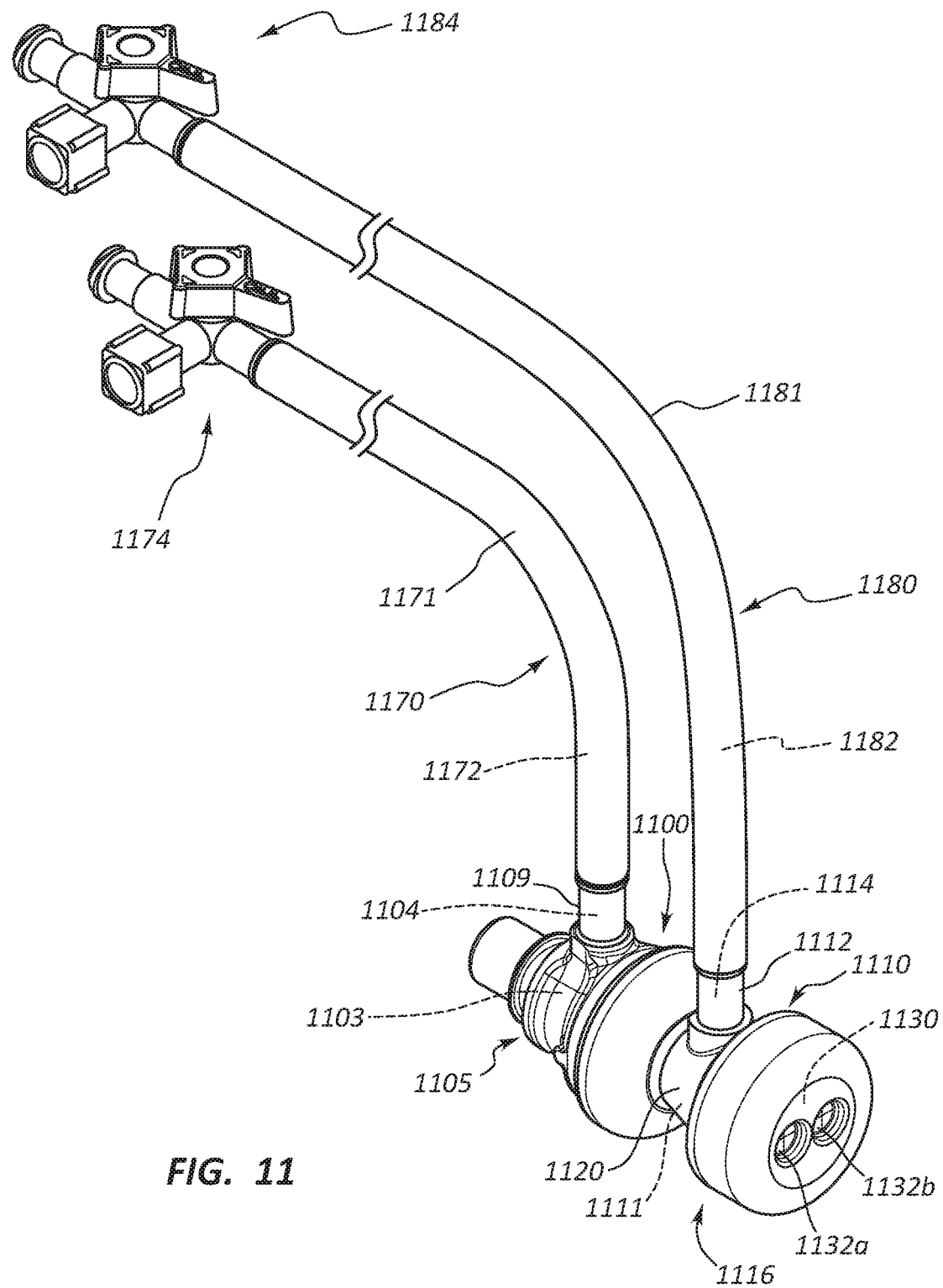
FIG. 11 is a perspective view of another embodiment of a hemostasis valve system.

FIG. 11 is a perspective view of a hemostasis valve system 1100. The hemostasis valve system 1100 can include a hemostasis valve 1110 and another medical device such as a first medical device 1105. The hemostasis valve 1110 can be releasably coupleable to the first medical device 1105. The first medical device 1105 may comprise or be releasably coupleable to a first elongate member 1170 including, for example, a length of tubing 1171 coupled to a stopcock 1174. The hemostasis valve 1110 may also comprise or be releasably coupleable to a second elongate member 1180 including, for example, a length of tubing 1181 coupled to a stopcock 1184. In certain embodiments, the first medical device 1105 may be independent of the first elongate member 1170 and/or the hemostasis valve 1110 may be independent of the second elongate member 1180. For example, the first medical device 1105 may be provided and/or used without the first elongate member 1170. Likewise, the hemostasis valve 1110 may be provided and/or used without the second elongate member 1180.

In some embodiments, the first medical device 1105 may be a traditional hemostasis valve, a valved sheath introducer, or another valved medical device. The first medical device 1105 may be an off-the-shelf medical device such that the tubing 1171 has a standard length. For example, the tubing 1171 of an off-the-shelf first medical device 1105 may be about 8 inches in length or another suitable length. In certain embodiments, the length of the tubing 1181 of the hemostasis valve 1110 may be greater than the length of the tubing 1171 of the first medical device 1105. For example, if the length of the tubing 1171 of the first medical device 1105 is 8 inches, the length of the tubing 1181 of the hemostasis valve 1110 may be between about 8.5 inches and about 9.5 inches, about 9 inches, between about 9.5 inches and about 10.5 inches, about 10 inches, between about 10.5 inches and about 11 inches, about 11 inches, or another suitable length. In certain other embodiments, the length of the tubing 1181 of the hemostasis valve 1110 may be less than the length of the tubing 1171 of the first medical device 1105. For example, if the length of the tubing 1171 of the first medical device 1105 is 8 inches, the length of the tubing 1181 of the hemostasis valve 1110 may be between about 6.5 inches and about 7.5 inches, about 7 inches, between about 5.5 inches and about 6.5 inches, about 6 inches, between about 4.5 inches and about 5.5 inches, about 5 inches, or another suitable length. Accordingly, the length of the tubing 1181 of the hemostasis valve 1110 may be an indicium. Stated another way, the length of the tubing 1181 of the hemostasis valve 1110 may be an indicium that communicates to a user which tubing is coupled to the hemostasis valve and which tubing is coupled to the first medical device 1105. The first and second lengths of the tubings 1171, 1181 can distinguish the tubings 1171, 1181 (and/or the first medical device 1105 and the hemostasis valve 1110) from each other. Other suitable indicia may also be used. For example, while the tubing 1171 of the first medical device may be clear or transparent, the tubing 1181 of the hemostasis valve 1110 may have a color or tint (e.g., the tubing 1181 may be green). Likewise, the stopcocks 1174, 1184 may be color coded to correspond with a portion of the hemostasis valve 1100, 1110 to which they are directly coupled.

The hemostasis valve 1110 can include a body 1120 and a valve member 1130. The valve member 1130 can be coupled to the body 1120 at a position at or adjacent a proximal end portion 1116 of the body 1120. The valve member 1130 may include a first sealable opening 1132a disposed through a first portion of the valve member 1130. The valve member 1130 may also include a second sealable opening 1132b disposed through a second portion of the valve member 1130. As discussed herein, a hemostasis valve having two or more sealable openings may aid in access and/or treatment. In certain embodiments, the valve member 1130 may include a third sealable opening, a fourth sealable opening, a fifth sealable opening, a sixth sealable opening, a seventh sealable opening, an eighth sealable opening, or more sealable openings.

With continued reference to FIG. 11, the hemostasis valve 1110 may further include a sidearm 1112. The sidearm 1112 may include a sidearm lumen 1114, the sidearm lumen 1114 extending through at least a portion of the sidearm 1112. In some embodiments, the sidearm lumen 1114 may be in fluid communication with a lumen or a hemostasis valve lumen 1111 of the hemostasis valve 1110. In various embodiments, the sidearm lumen 1114 may be in fluid communication with a lumen or a second elongate member lumen 1182 of the second elongate member 1180.

The first medical device 1105 may also include a sidearm 1109. The sidearm 1109 may include a sidearm lumen 1104, the sidearm lumen 1104 extending through at least a portion of the sidearm 1109. In some embodiments, the sidearm lumen 1104 may be in fluid communication with a lumen or a first medical device lumen 1103 of the first medical device 1105. In certain embodiments, the sidearm lumen 1104 may be in fluid communication with a lumen or a first elongate member lumen 1172 of the first elongate member 1170. As shown, the first elongate member 1170 may be coupled or releasably coupled to the sidearm 1109 and the second elongate member 1180 may be coupled or releasably coupled to the sidearm 1112.

As discussed above, the sidearm 1112 may rotate independent of the sidearm 1109, for example, when the hemostasis valve 1110 is coupled to the first medical device 1105. The hemostasis valve 1110 may also be configured such that upon coupling of the hemostasis valve 1110 to the first medical device 1105, the sidearm lumen 1104 is not blocked by a portion of the hemostasis valve 1110. In various embodiments, each of the first and second elongate member lumens 1172, 1182 may be in fluid communication with each of the first medical device lumen 1103 and the hemostasis valve lumen 1111 (e.g., when the first medical device 1105 comprising the first elongate member 1170 is coupled to the hemostasis valve 1110 comprising the second elongate member 1180).

Methods of using the hemostasis valve systems and hemostasis valves are also disclosed herein. In some embodiments, a method of using a hemostasis valve system or hemostasis valve as disclosed herein may include displacing a first elongate medical device (e.g., a first guidewire) through a first sealable opening of the hemostasis valve. The method may further include displacing a second elongate medical device (e.g., a second guidewire) through a second sealable opening of the hemostasis valve.

In certain embodiments, the method of using the hemostasis valve system or hemostasis valve may include coupling the hemostasis valve to a valved medical device (e.g., another hemostasis valve) such that a lumen of the hemostasis valve is in fluid communication with a lumen of the valved medical device, and such that the hemostasis valve bypasses the valve of the valved medical device. In various embodiments, the hemostasis valve may be sealably coupled to the valved medical device.

Additional methods and/or method steps can be derived from FIGS. 1A-7B and the corresponding disclosure. Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially sealed" is recited with respect to a feature, it is understood that in further embodiments, the feature can have a precisely sealed configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, which changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A hemostasis valve comprising:
   a body;
   a valve member coupled to the body, the valve member comprising:
   a first sealable opening disposed through a first portion of the valve member;
   a first edge surrounding the first sealable opening, the first edge being sloped;
   a second sealable opening disposed through a second portion of the valve member;
   a second edge surrounding the second sealable opening, the second edge being sloped;
   a continuous slit disposed through at least a portion of the first sealable opening and through at least a portion of the second sealable opening; and
   a valve dividing member comprising an elongate member that is configured to divide the first sealable opening from the second sealable opening,
   wherein the elongate member is disposed between the first sealable opening and the second sealable opening, is disposable substantially perpendicular to the continuous slit, and is laterally movable along the continuous slit; and
   a single hemostasis valve lumen extending between a proximal end portion and a distal end portion of the hemostasis valve.

2. The hemostasis valve of claim 1, wherein the valve member further comprises a resilient wall disposed between the first sealable opening and the second sealable opening.

3. The hemostasis valve of claim 1, wherein the body further comprises a sidearm, the sidearm comprising a sidearm lumen extending therethrough, the sidearm lumen in fluid communication with the single hemostasis valve lumen.

4. The hemostasis valve of claim 3, further comprising an additional elongate member coupled to the sidearm, the additional elongate member comprising an elongate member lumen extending therethrough.

5. The hemostasis valve of claim 1, further comprising: a valve bypass portion extending distally from the distal end portion of the hemostasis valve, wherein the single hemostasis valve lumen further extends through a portion of the valve bypass portion.

6. The hemostasis valve of claim 5, wherein the valve bypass portion is configured to bypass a valve of a valved medical device when the hemostasis valve is coupled to the valved medical device such that the hemostasis valve is in fluid communication with the valved medical device.

7. The hemostasis valve of claim 1, further comprising indicia configured to designate at least one of the first sealable opening and the second sealable opening.

8. The hemostasis valve of claim 1, wherein the valve dividing member further comprises a second elongate member, and
   wherein the elongate member is disposed on a first side of the valve member and the second elongate member is disposed on a second side of the valve member.

9. A hemostasis valve system comprising:
   a hemostasis valve comprising:
   a body;
   a valve member coupled to a proximal end portion of the body, the valve member comprising a first sealable opening disposed through a first portion of the valve member, a first edge surrounding the first sealable opening, the first edge being sloped, a second sealable opening disposed through a second portion of the valve member, and a second edge surrounding the second sealable opening, the second edge being sloped;
   a continuous slit disposed through at least a portion of the first sealable opening and through at least a portion of the second sealable opening; and
   a valve dividing member comprising an elongate member that is configured to divide the first sealable opening from the second sealable opening,
   wherein the elongate member is disposed between the first sealable opening and the second sealable opening, is disposable substantially perpendicular to the continuous slit, and is laterally movable along the continuous slit; and
   a single hemostasis valve lumen extending between the proximal end portion and a distal end portion of the hemostasis valve; and a first medical device comprising a valve, wherein the hemostasis valve is releasably coupleable to the first medical device;

wherein the single hemostasis valve lumen comprises a sloped portion disposed between the valve member and the valve of the first medical device, wherein the sloped portion comprises a first diameter and a second diameter distal of the first diameter, and wherein the second diameter is less than the first diameter.

10. The hemostasis valve system of claim 9, further comprising:
a valve bypass portion extending distally from the distal end portion of the hemostasis valve, wherein the single hemostasis valve lumen further extends through a portion of the valve bypass portion.

11. The hemostasis valve system of claim 10, wherein the valve bypass portion is configured to bypass the valve of the first medical device when the valve bypass portion is displaced through the valve of the first medical device.

12. The hemostasis valve system of claim 9, wherein the body of the hemostasis valve further comprises a sidearm, the sidearm of the hemostasis valve comprising a sidearm lumen extending therethrough, the sidearm lumen in fluid communication with the single hemostasis valve lumen; and
wherein the first medical device comprises a sidearm, the sidearm of the first medical device comprising a sidearm lumen extending therethrough.

13. The hemostasis valve system of claim 12, wherein the sidearm of the hemostasis valve and the sidearm of the first medical device are aligned with the first sealable opening and the second sealable opening.

14. The hemostasis valve system of claim 12, further comprising:
a first elongate member coupled to the sidearm of the first medical device, the first elongate member having a first length; and
a second elongate member coupled to the sidearm of the hemostasis valve, the second elongate member having a second length.

15. The hemostasis valve system of claim 14, wherein the first length is greater than the second length.

16. The hemostasis valve system of claim 14, wherein the first length is less than the second length.

17. The hemostasis valve system of claim 14, wherein the first length is an indicium that communicates the position of the first elongate member and the first medical device to a user.

18. The hemostasis valve system of claim 9, further comprising:
a cap coupled to the proximal end portion of the body of the hemostasis valve such that a portion of the cap is disposed proximal of the valve member, the cap comprising a first cap opening disposed in substantial alignment with the first sealable opening and a second cap opening disposed in substantial alignment with the second sealable opening.

* * * * *